(12) United States Patent
Shaked

(10) Patent No.: US 7,766,951 B2
(45) Date of Patent: Aug. 3, 2010

(54) VESSEL TREATMENT DEVICES

(75) Inventor: Yoav Shaked, Tzoran (IL)

(73) Assignee: Y Med, Inc., Tempe, AZ (US)

( * ) Notice: Subject to any disclaimer, the term of this patent is extended or adjusted under 35 U.S.C. 154(b) by 1265 days.

(21) Appl. No.: 11/240,631

(22) Filed: Oct. 3, 2005

(65) Prior Publication Data

US 2006/0106448 A1    May 18, 2006

Related U.S. Application Data

(63) Continuation-in-part of application No. 11/070,294, filed on Mar. 3, 2005, now Pat. No. 7,438,720, which is a continuation-in-part of application No. 10/899,034, filed on Jul. 27, 2004, now abandoned.

(60) Provisional application No. 60/549,554, filed on Mar. 4, 2004.

(51) Int. Cl.
*A61F 2/06* (2006.01)
(52) U.S. Cl. .................................... 623/1.11
(58) Field of Classification Search ....... 623/1.11–1.15, 623/1.35, 1.36; 606/191–198; 601/101.01–101.03
See application file for complete search history.

(56) References Cited

U.S. PATENT DOCUMENTS

| | | | |
|---|---|---|---|
| 4,983,167 A | 1/1991 | Sahota | |
| 5,462,530 A | 10/1995 | Jang | |
| 5,685,847 A | 11/1997 | Barry | |
| 5,749,825 A | 5/1998 | Fischell | |
| 6,048,361 A | 4/2000 | Von Oepen | |
| 6,375,660 B1 | 4/2002 | Fischell | |
| 6,428,567 B2 * | 8/2002 | Wilson et al. | 623/1.11 |
| 6,440,097 B1 | 8/2002 | Kupiecki | |
| 6,508,836 B2 | 1/2003 | Wison | |
| 6,579,312 B2 | 6/2003 | Wilson | |
| 6,682,556 B1 | 1/2004 | Ischinger | |
| 6,692,483 B2 | 2/2004 | Vardi | |
| 7,314,480 B2 * | 1/2008 | Eidenschink et al. | 623/1.11 |
| 2001/0049548 A1 | 12/2001 | Vardi et al. | |
| 2002/0091434 A1 | 7/2002 | Chambers | |
| 2002/0147491 A1 | 10/2002 | Khan et al. | |
| 2003/0055483 A1 | 3/2003 | Gumm | |
| 2003/0074046 A1 | 4/2003 | Richter | |
| 2003/0074047 A1 | 4/2003 | Richter | |
| 2003/0114912 A1 | 6/2003 | Sequin et al. | |
| 2003/0187494 A1 | 10/2003 | Loaldi | |
| 2003/0191436 A1 * | 10/2003 | Horvers | 606/192 |
| 2004/0098087 A1 | 5/2004 | Madrid et al. | |
| 2004/0138734 A1 | 7/2004 | Chobotov | |
| 2004/0172121 A1 | 9/2004 | Eidenschink et al. | |
| 2005/0015135 A1 | 1/2005 | Shanley | |

* cited by examiner

*Primary Examiner*—Kevin T Truong
(74) *Attorney, Agent, or Firm*—Rutan & Tucker, LLP

(57) ABSTRACT

A catheter system for treating lesions is provided. The system is suitable for treatment of bifurcation lesions, has a low profile and provides substantially predictable translational and rotational positioning. In one embodiment, the system includes a fixed wire balloon catheter and a partially attached guidewire lumen, wherein the guidewire lumen is attached to the catheter at a crotch point. The location of the crotch point is predetermined so as to provide substantially predictable positioning. Several embodiments of the system are described for various types of lesions and vessel configurations.

8 Claims, 18 Drawing Sheets

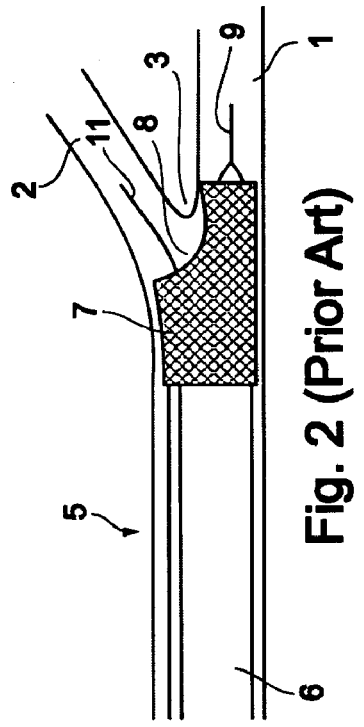
Fig. 1
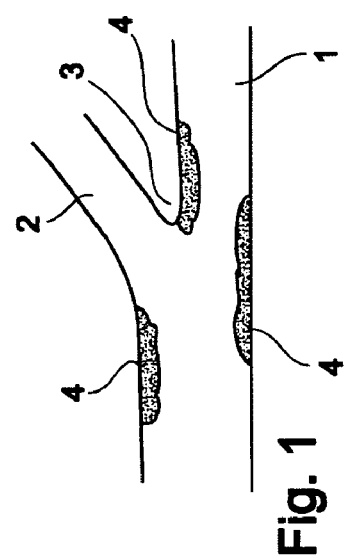
Fig. 2 (Prior Art)
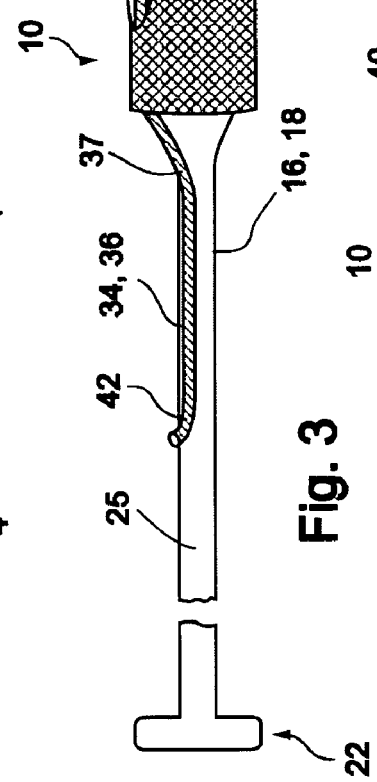
Fig. 3
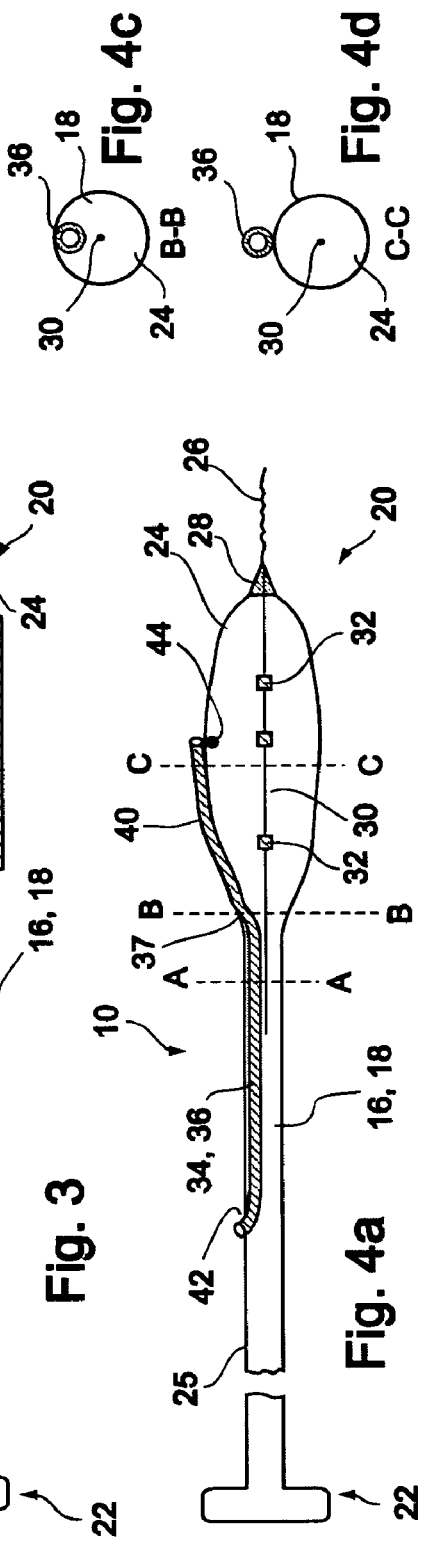
Fig. 4a
Fig. 4b
Fig. 4c
Fig. 4d

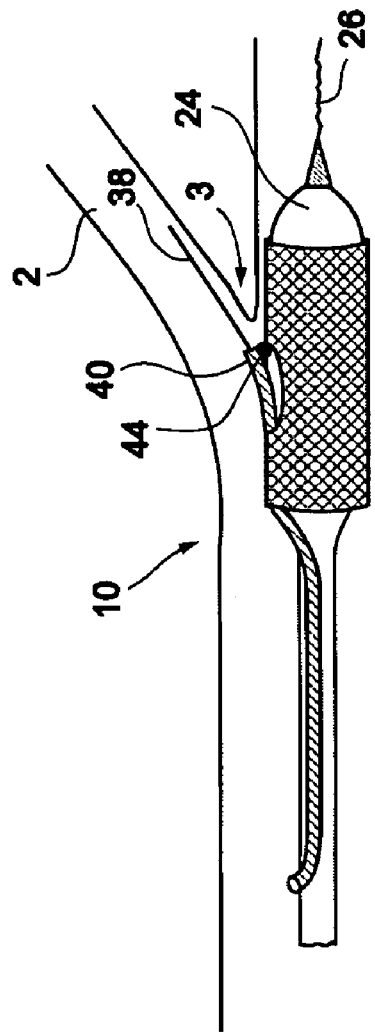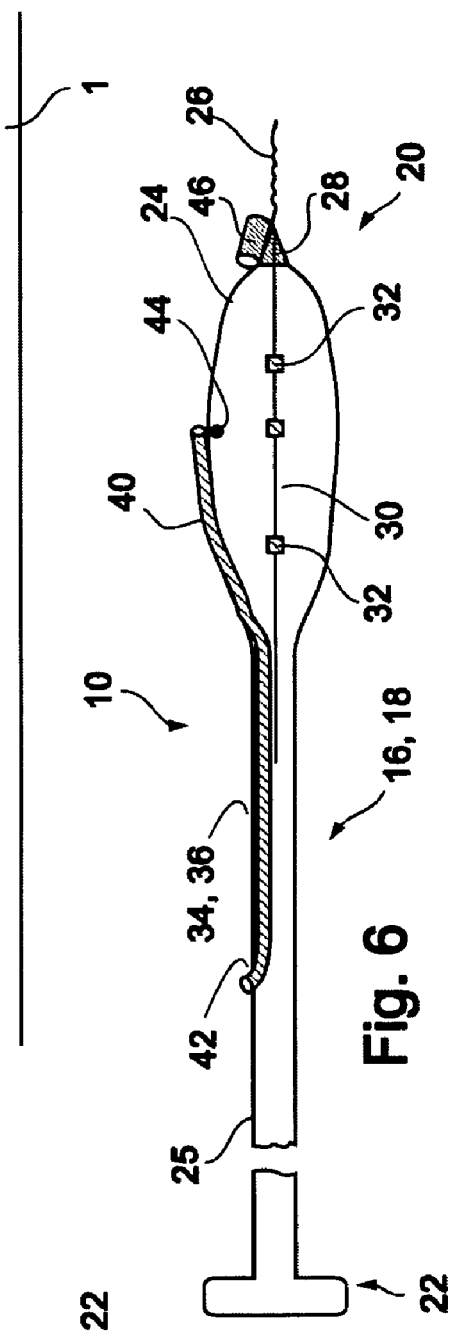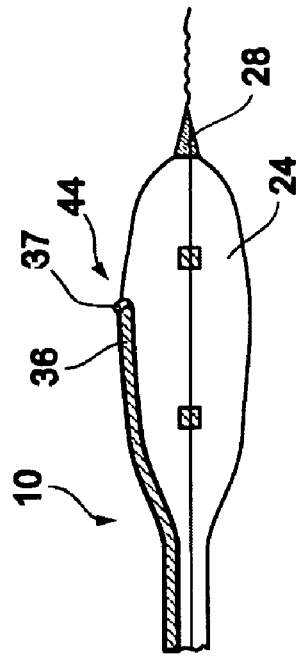

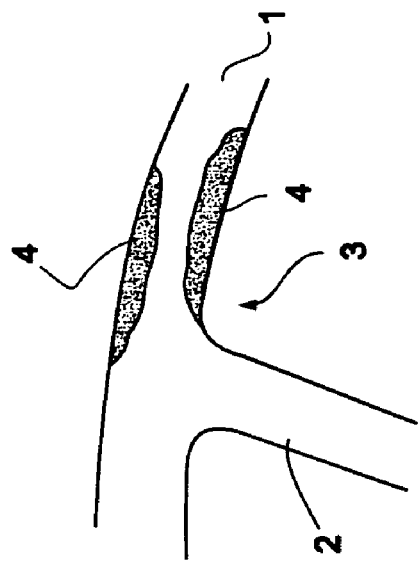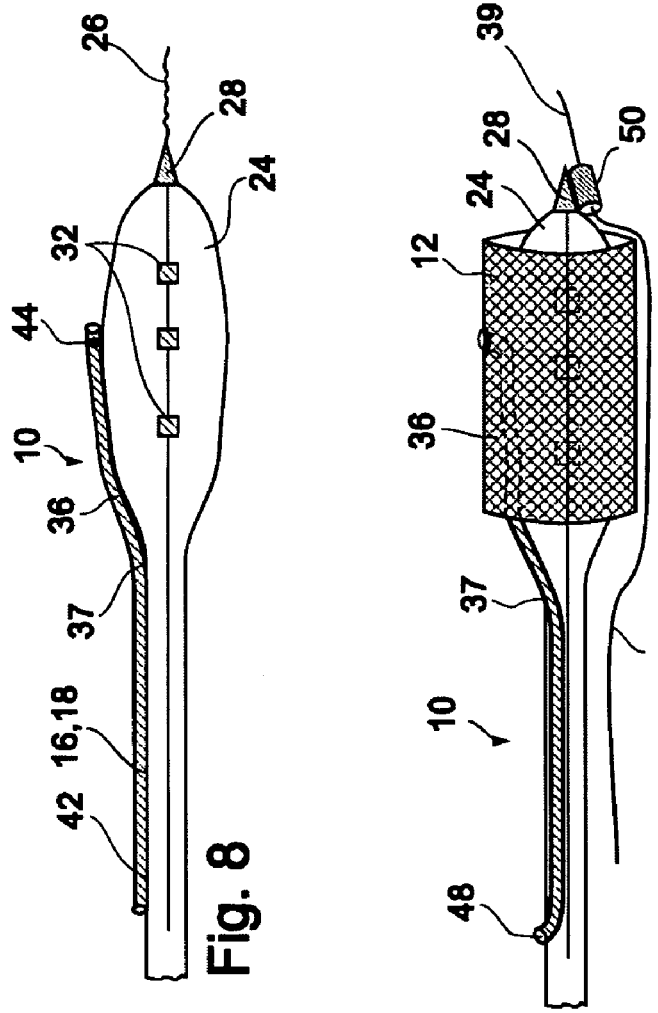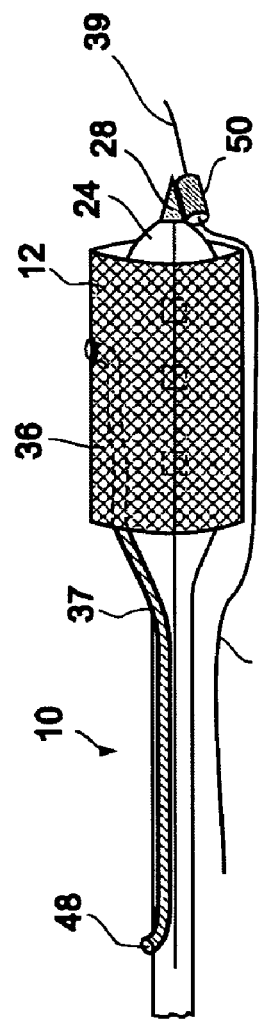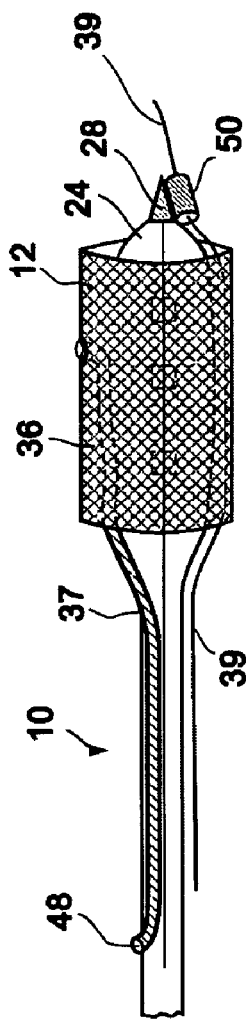

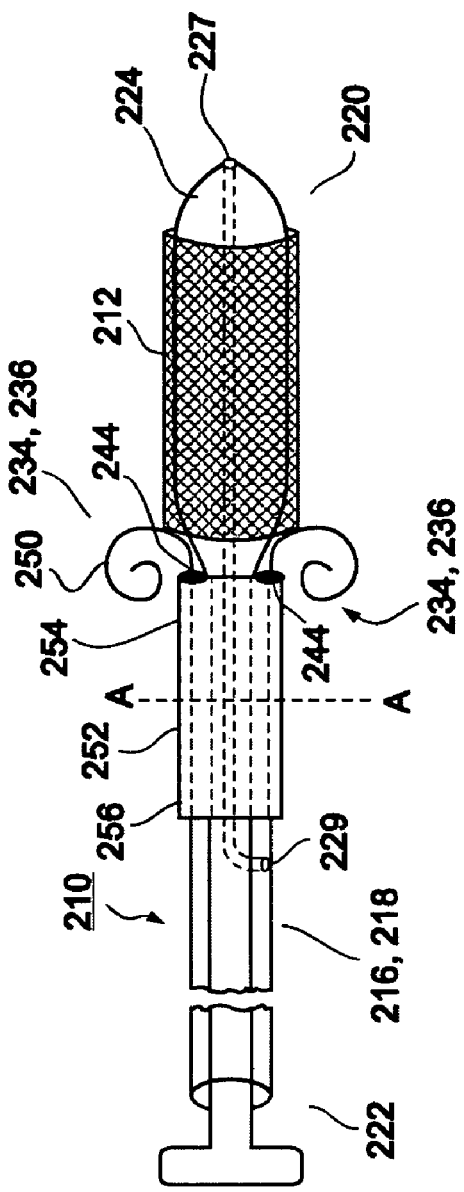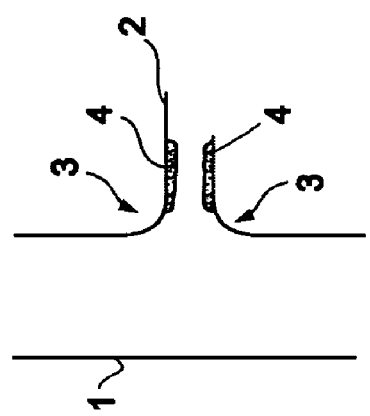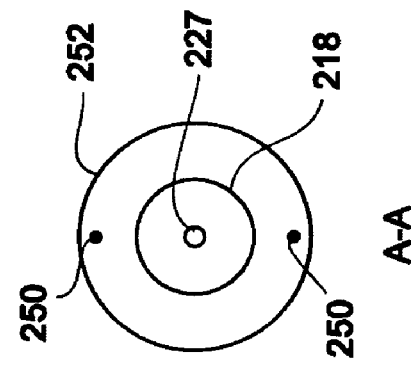
Fig. 14a
Fig. 13
Fig. 14b

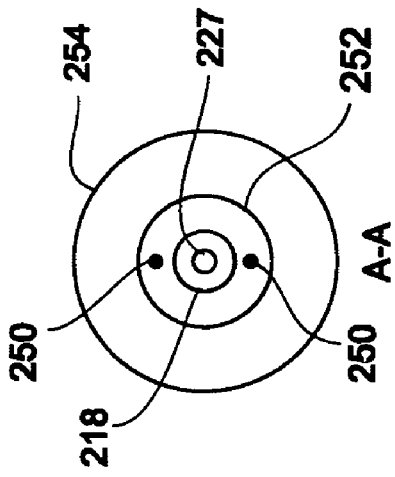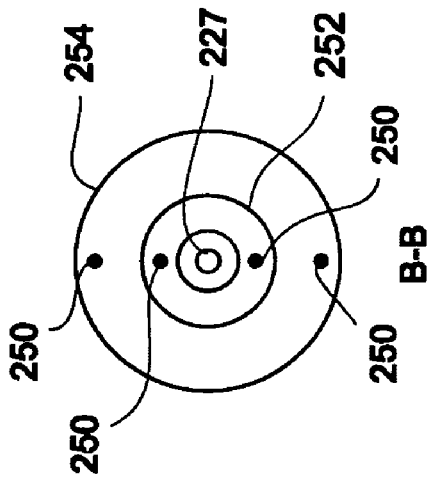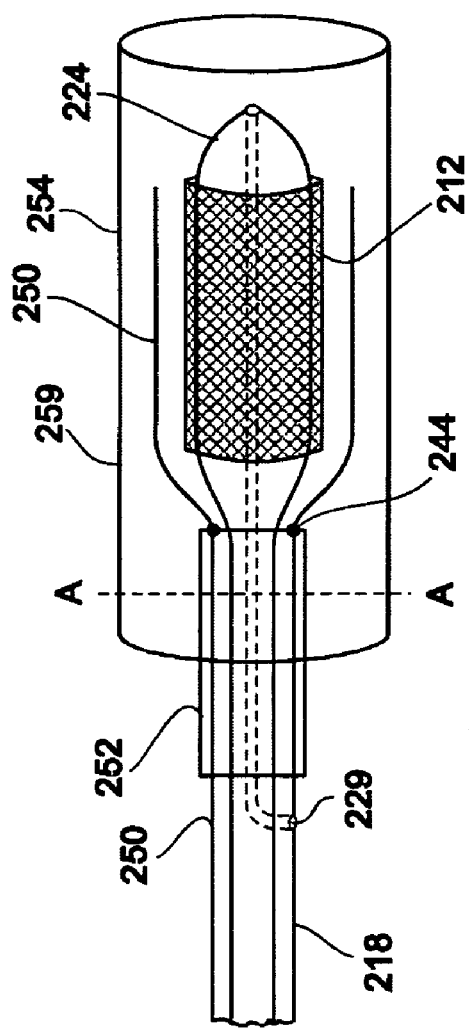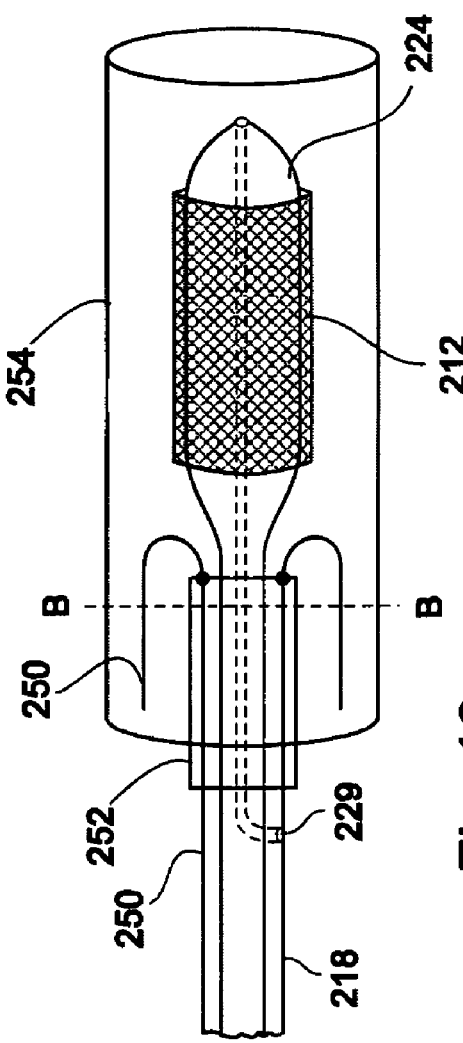

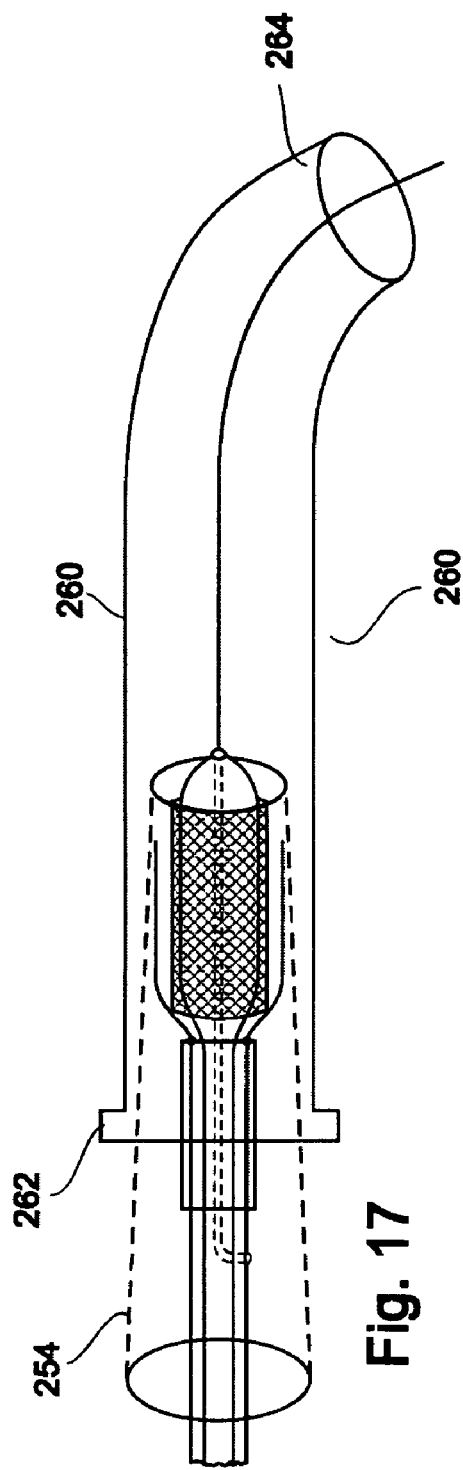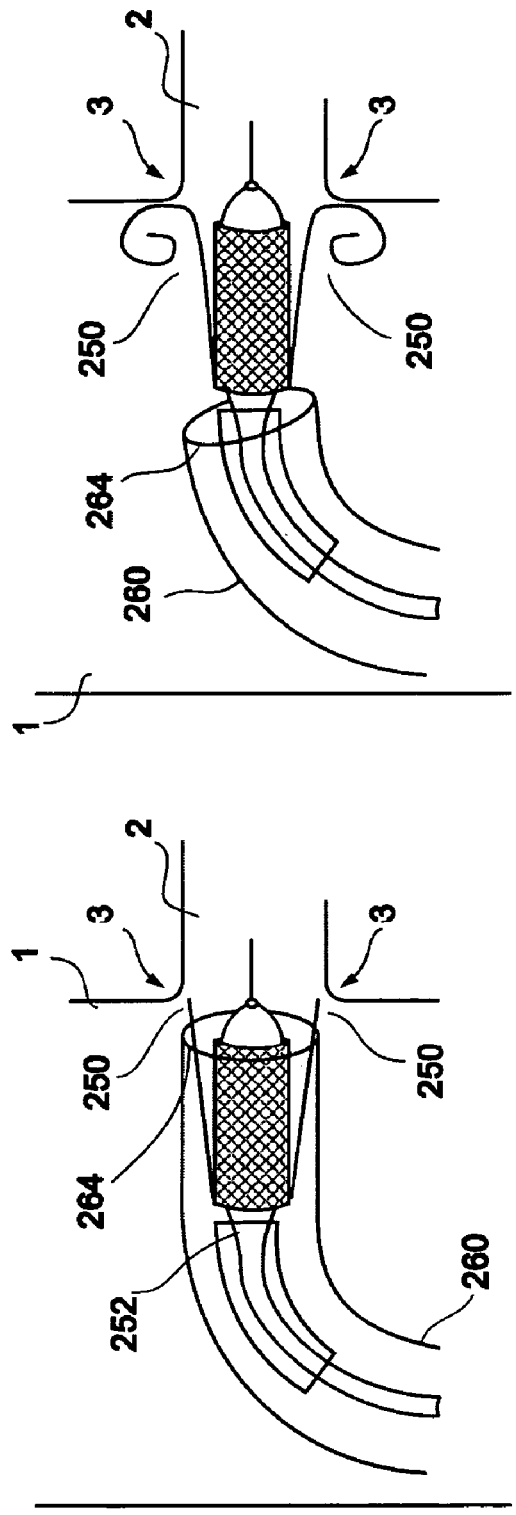

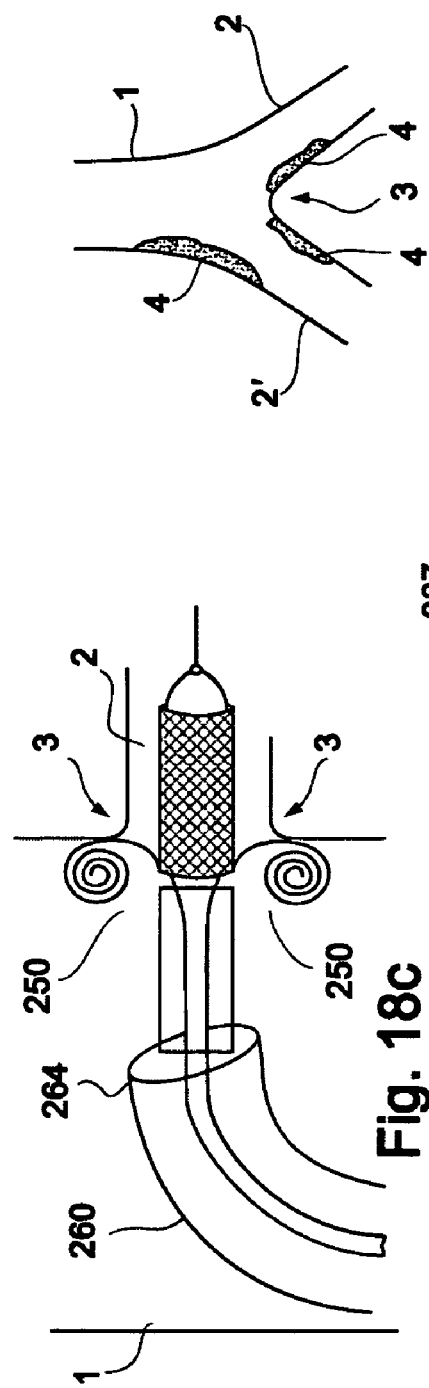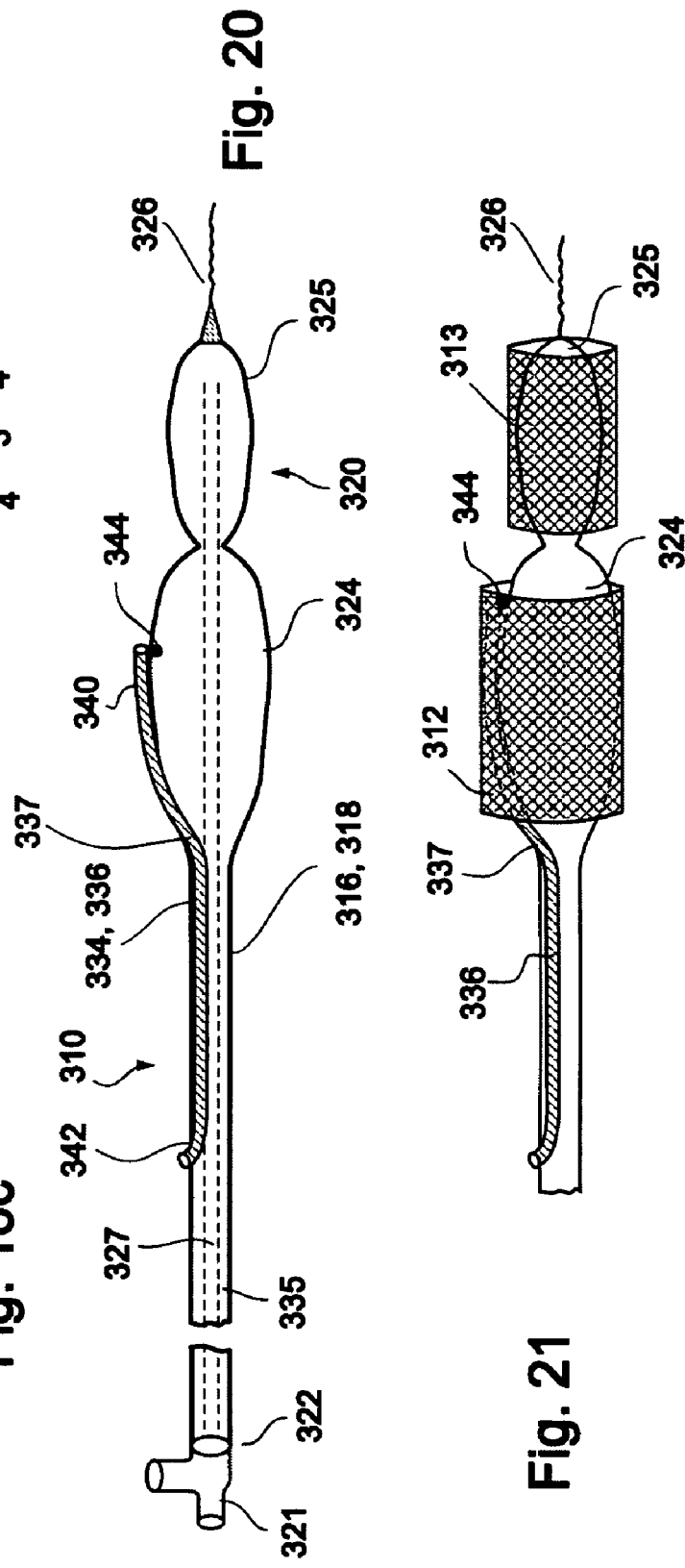

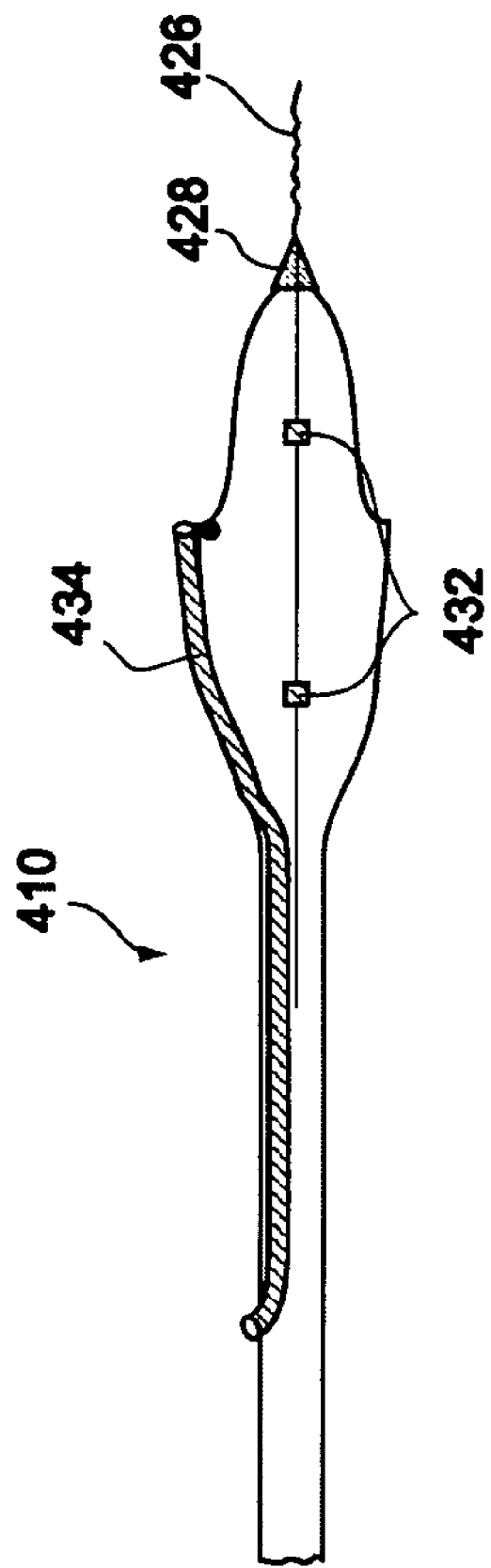

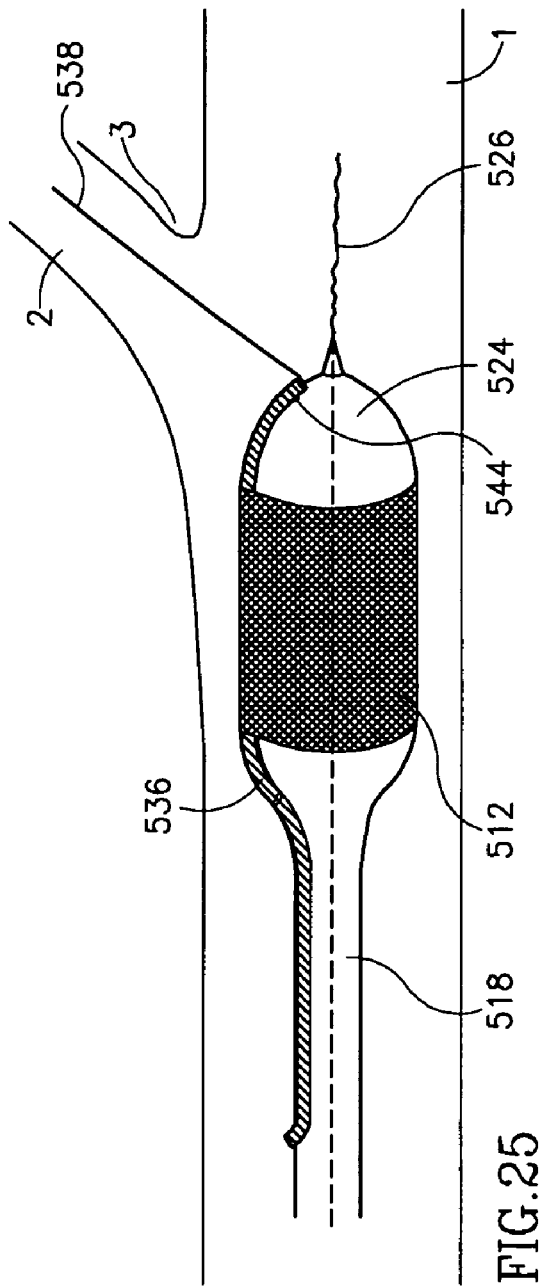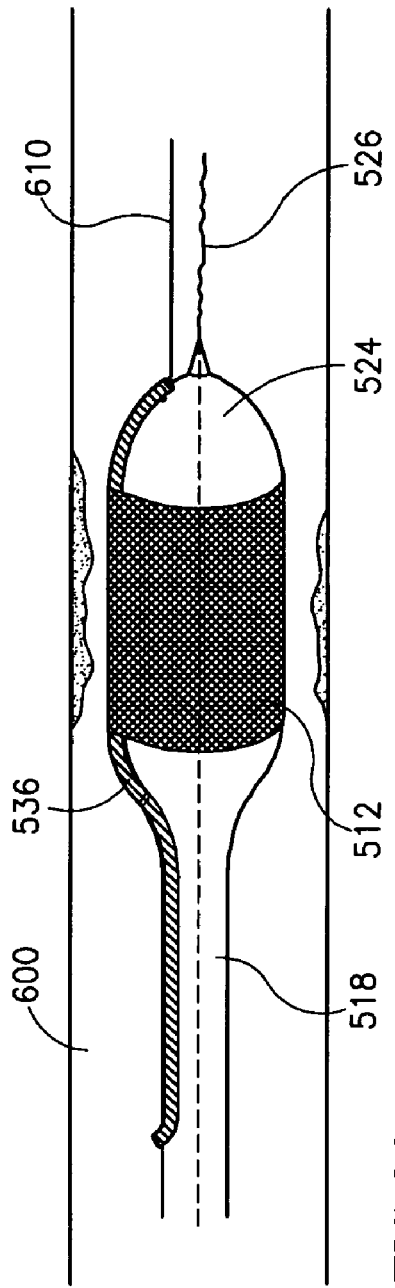
FIG. 25
FIG. 26

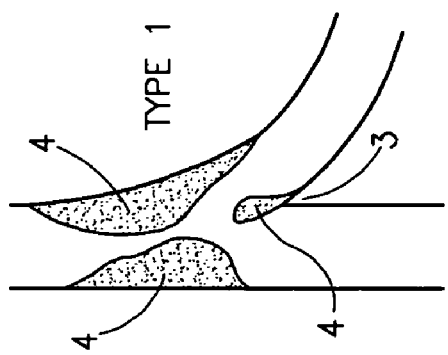
FIG.29a TYPE 1
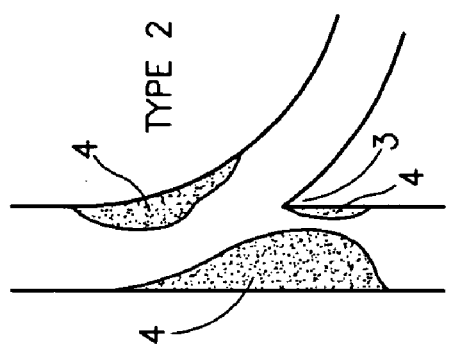
FIG.29b TYPE 2
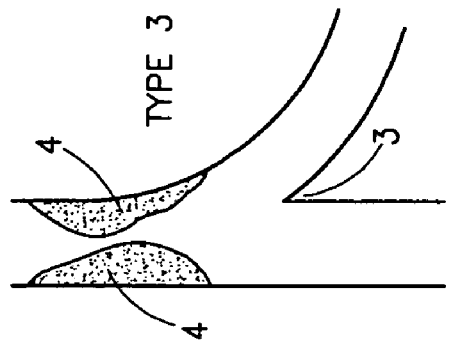
FIG.29c TYPE 3
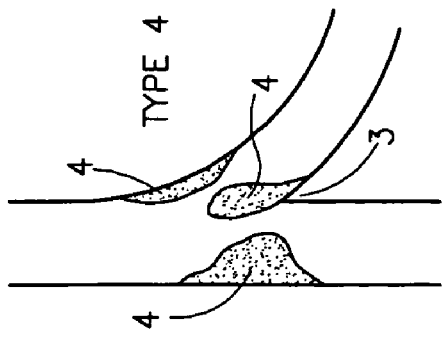
FIG.29d TYPE 4
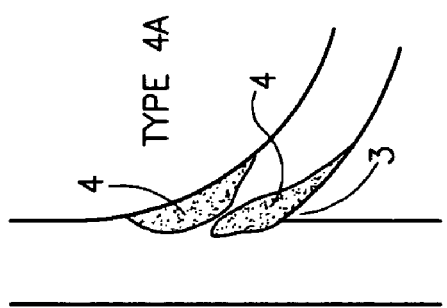
FIG.29e TYPE 4A
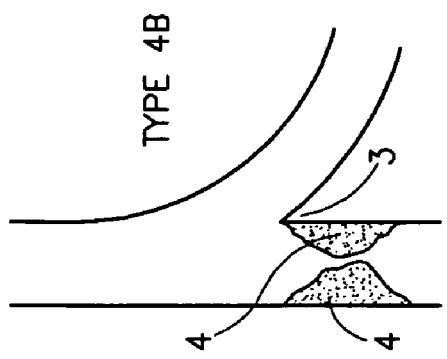
FIG.29f TYPE 4B

VESSEL TREATMENT DEVICES

CROSS-REFERENCE TO RELATED APPLICATIONS

This application is a continuation-in-part application of U.S. patent application Ser. No. 11/070,294, filed on Mar. 3, 2005 now U.S. Pat. No. 7,438,720, which is a continuation-in-part application of U.S. patent application Ser. No. 10/899,034, filed on Jul. 27, 2004 now abandoned, which claims the benefit of U.S. Provisional Application No. 60/549,554, filed on Mar. 4, 2004, all of which are incorporated herein by reference in their entireties.

FIELD AND BACKGROUND OF THE INVENTION

The present invention relates to vessel treatment devices and methods and, more particularly, to catheter systems having low profiles and predictable positioning capabilities, both rotationally and translationally.

Several problems are associated with known prior art stent delivery devices, particularly ones which are suitable for treating bifurcation lesions. First, they generally have large outer diameters, particularly since the known designs usually include two guidewire lumens—one for a main guidewire and one for a side branch guidewire. The relatively large profiles of currently known systems cause difficulties in maneuverability and access to the site. Furthermore, the presence of two guidewires often results in wire entanglement, making the procedure difficult to perform without multiple insertions and retractions. Another problem which persists in these devices is inaccurate positioning within the vessel. This problem has been addressed with the use of radiopaque markers placed in strategic locations. However, visualization is done in the two-dimensional plane, while the actual procedure takes place within the three-dimensional realm. As such, inaccurate deployment is commonplace, often resulting in either stent jailing or insufficient coverage.

An example of a prior art bifurcation stent delivery system is disclosed in U.S. Pat. No. 6,048,361 to Von Oepen. The system includes a stent with an increased radial opening and a balloon catheter on which the stent is mounted, the balloon catheter having a hollow chamber for passage of a guiding wire so that it exits in a center of the increased opening. The system disclosed therein includes two passageways for guidewires, necessitating a relatively large outer diameter. Furthermore, the presence of two wires can lead to problems of wire entanglement.

Other examples of prior art bifurcation stent delivery systems and methods are disclosed in U.S. Pat. No. 6,692,483 to Vardi et al. and U.S. Publication Number 2001/0049548 to Vardi et al. These include a balloon catheter having a main guidewire lumen and a flexible side sheath having a side branch lumen. The method disclosed aims to reduce wire entanglement by first inserting one of the guidewires, then advancing the system, and finally advancing the second guidewire. Alternatively, one of the guidewires is housed within the system and only released once the system is in place. However, problems of wire entanglement may also occur upon removal of the system. Furthermore, the system disclosed therein is prone to overshooting of the bifurcation, resulting in sub-optimal placement. Finally, the dual lumen configuration results in a relatively large profile for the overall system.

Other similar examples of prior art bifurcation stent delivery systems are disclosed in U.S. Pat. No. 5,749,825 to Fischell et al. and U.S. Pat. No. 6,682,556 to Ischinger. The systems disclosed therein include balloon catheters with side branch tubes, and require two guidewires: one for the main vessel and one for the branch vessel. Similar to the aforementioned prior art, large profile, wire entanglement, and inaccurate positioning are potential problems.

A prior art device which aims to provide improved rotational orientation while avoiding wire entanglement is disclosed in U.S. Publication Number 2003/0055483 to Gumm. Gumm discloses a catheter assembly having a rotatably mounted balloon, and further including a side branch hollow member attached to the catheter balloon. A noted feature of the device is the use of rotating members sealed to opposite ends of the balloon. Thus, the side branch hollow member, the balloon and the rotating members act as a unit which rotates freely relative to the main hypotube. This particular feature is considered an integral part of the design, providing improved orientation of the stent relative to the side branch at the bifurcation. However, this feature also results in an increased overall diameter of the system. Furthermore, it does not provide a way to accurately position the stent in the translational plane.

Attempts have been made to reduce the profile of a single stent delivery device by using a fixed wire balloon catheter, such as is disclosed in U.S. Publication Number 2002/0147491 to Khan et al. The device disclosed therein includes either a short section of guidewire fixedly attached to the distal end of a balloon, or a core wire that extends within the system. This design reduces the profile of the system as compared to prior art devices by eliminating the inner guidewire lumen. However, the system disclosed therein does not teach or suggest the possibility of bifurcation stenting, nor does it provide rapid exchange capabilities.

There is thus a widely recognized need for, and it would be highly advantageous to have, a stent delivery system devoid of the above limitations.

SUMMARY OF THE INVENTION

According to the present invention, there is provided a catheter system including a catheter body with a catheter proximal end and a catheter distal end, a balloon positioned on the catheter distal end, the balloon having a balloon proximal end and a balloon distal end, a guidewire lumen attached to the balloon distal end, the guidewire lumen having a length of less than 15 mm, and a guidewire enclosure having an enclosure distal end and an enclosure proximal end, and at least partially attached to the catheter body.

According to further features in preferred embodiments, the catheter system further includes a stent positioned on the balloon. The stent has either a dedicated side opening or regular openings, and the enclosure distal end is positionable at or through the side opening or openings. In a preferred embodiment, the balloon in its deflated configuration has a temporary lumen for receiving a guidewire therethrough, and the temporary lumen is preferably longitudinally aligned with the guidewire lumen, such that a distal end of the guidewire is positionable through the guidewire lumen and a portion of the guidewire which is proximal to the distal end of the guidewire is positionable in the temporary lumen. According to further features, the balloon in a deflated configuration has an "S" shape having an upper curved portion and a lower curved portion, wherein the lower curved portion is a containment area for holding a guidewire therein. In alternative embodiments, the balloon in a deflated configuration has a hooked "Y" shape, wherein a bottom portion of the "Y" shape is hooked so as to form a containment area for holding a guidewire therein. The "Y" shape may further include two upper arms which form a secondary containment area for holding the guidewire enclosure therein. In a preferred embodiment, the temporary lumen and the guidewire lumen are on an opposite side from the guidewire enclosure. According to additional features, the guidewire enclosure is at least partially positioned within the catheter body and is attached to the catheter body at a location on the balloon. The location of attachment is approximately in a center of the balloon.

According to a further aspect of the present invention, there is provided a method for treating a lesion in a vessel. The method includes providing a catheter system having a catheter body with a balloon on a distal end thereof, a guidewire lumen attached to a distal end of the balloon, a guidewire enclosure at least partially attached to the catheter; and a guidewire positioned through the guidewire lumen and through a temporary lumen in the balloon such that the guidewire is immovable with respect to the catheter body, introducing a tracking guidewire having a distal end and a proximal end into the vessel, positioning the proximal end of the tracking guidewire in the guidewire enclosure, advancing the catheter over the tracking guidewire until the catheter reaches the lesion, and inflating the balloon thereby releasing the guidewire from the temporary lumen.

According to yet another aspect of the invention, there is provided a catheter system including a catheter body having a catheter proximal end and a catheter distal end, a fixed wire balloon positioned at the catheter distal end and having a working length portion having a substantially uniform diameter, a proximal narrowed portion proximal to the working length portion having a smaller diameter than the substantially uniform diameter of the working length portion, and a distal narrowed portion distal to the working length portion having a smaller diameter than the substantially uniform diameter of the working length portion, and a guidewire enclosure having an enclosure proximal end and an enclosure distal end, the guidewire enclosure at least partially attached to the catheter at an attachment point, wherein the attachment point is located proximal to said working length portion of said fixed wire balloon.

According to further features in preferred embodiments of the present invention, the guidewire enclosure is at least partially positioned within the catheter body. The attachment point is at or proximal to the enclosure distal end. In one preferred embodiment, the catheter system further includes a guidewire positionable within the guidewire enclosure. According to further features, at least a portion of the catheter body is comprised of a rigid material thereby providing a rigid control area, and the catheter system further includes a substantially rigid core wire positioned through the fixed wire balloon and connecting the balloon distal end and the rigid control area.

According to yet another aspect of the present invention, there is provided a method for treating a lesion in a vessel. The method includes introducing a guidewire into the vessel and through the lesion, providing a catheter having a fixed wire balloon and a guidewire enclosure attached to a proximal end of the fixed wire balloon, introducing a proximal end of the guidewire into the guidewire enclosure of the catheter, advancing the catheter over the guidewire until a distal end of the catheter is at the lesion and the guidewire is positioned alongside the balloon, and inflating the balloon so as to compress the guidewire into the lesion.

In one embodiment, the method further includes treating a lesion in a second vessel, the second vessel being connected to the first vessel at a bifurcation. The method includes at least partially deflating the balloon, retracting the catheter along the guidewire, introducing the catheter into the second vessel, and inflating the balloon.

According to yet another aspect of the invention there is provided a method for treating a first lesion in a first vessel and a second lesion in a second vessel, the first and second vessel connected at a bifurcation. The method includes introducing a guidewire into the second vessel, providing a catheter having a fixed wire balloon and a guidewire enclosure attached to a proximal end of the fixed wire balloon, introducing a proximal end of the guidewire into the guidewire enclosure of the catheter, advancing the catheter over the guidewire until a distal end of the catheter reaches the bifurcation, further advancing the catheter past the bifurcation and into the first vessel such that the balloon is positioned alongside the first lesion, inflating the balloon, deflating the balloon, retracting the catheter over the guidewire, introducing the catheter into the second vessel, such that the guidewire is positioned alongside the balloon, and inflating the balloon so as to compress the guidewire into the second lesion.

According to yet another aspect of the invention, there is provided a method for treating an intracranial aneurysm in a vessel. The method includes providing a catheter having a fixed wire balloon, an auxiliary elongated element at least partially attached to the balloon, and a stent positioned on the balloon and having a side opening, wherein the elongated element is positioned at the side opening, introducing the catheter into the vessel, positioning the catheter such that said the side opening is situated at the aneurysm, deploying the stent, removing the catheter, and introducing a coil delivery system for introduction of an embolic coil into the aneurysm.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is an illustration of a first type of vessel bifurcation with plaque buildup;

FIG. 2 is an illustration of a prior art bifurcation stent delivery system;

FIG. 3 is an illustration of a bifurcation stent delivery system in accordance with a preferred embodiment of the present invention;

FIGS. 4a-d are illustrations of the system of FIG. 3 shown without a stent;

FIG. 5 is an illustration of the system of FIG. 3 in position at a bifurcation;

FIG. 6 is an illustration of a the system of FIG. 3, shown without a stent, and further including a distal connecting element;

FIG. 7 is an illustration of a bifurcation stent delivery system, shown without a stent, in accordance with another embodiment of the present invention;

FIG. 8 is an illustration of a bifurcation stent delivery system, shown without a stent, in accordance with yet another embodiment of the present invention;

FIGS. 9a and 9b are illustrations of a bifurcation stent delivery system in accordance with another embodiment of the present invention;

FIG. 10 is an illustration of a second type of vessel bifurcation with plaque buildup;

FIG. 13 is an illustration of a third type of vessel bifurcation with plaque buildup;

FIGS. 14a and b are illustrations of a system for treating a bifurcation such as the one depicted in FIG. 13;

FIGS. 15a and b are illustrations of the system of FIG. 14, further including a holder;

FIGS. 16a and b are illustrations of the system of FIG. 14, further including a holder, in an alternative embodiment;

FIG. 17 is an illustration of the system of FIG. 14 being introduced into a guiding catheter;

FIGS. 18a-c are illustrations of the system of FIG. 14 during positioning and deployment;

FIG. 19 is an illustration of a fourth type of vessel bifurcation with plaque buildup;

FIG. 20 is an illustration of a system, shown without a stent, for treating a bifurcation such as the one depicted in FIG. 19;

FIG. 21 is an illustration of the system depicted in FIG. 20, further including stents thereon;

FIG. 23 is an illustration of a tapered balloon system with a side branch lumen, in accordance with another embodiment of the present invention;

FIG. 25 is an illustration of the system of FIG. 24a in place at a bifurcation;

FIG. 26 is an illustration of the system of FIG. 24a in place at a non-bifurcated lesion;

FIGS. 29a-f are illustrations of different types of bifurcation lesions;

DESCRIPTION OF THE PREFERRED EMBODIMENTS

Figure 11A:
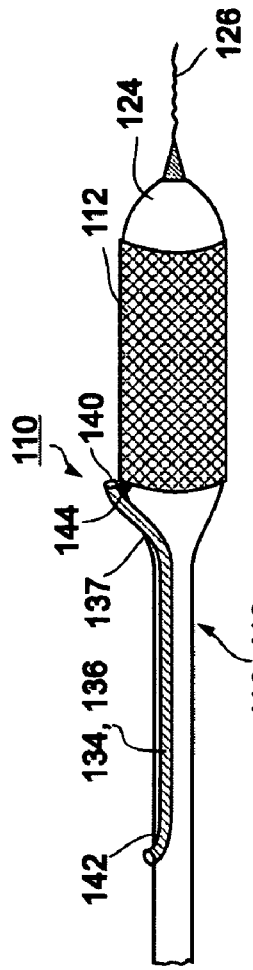
FIGS. 11a-c are illustrations of a system for treating a bifurcation such as the one depicted in FIG. 10.

The present invention is of a catheter systems and methods. Specifically, the present invention can be positioned in a vessel with rotational and translational alignment. In addition to providing substantially predictable alignment, the devices and systems of the present invention have small outer diameters as compared with prior art systems, particularly ones which are suitable for treating a bifurcation, and reduce the possibility of wire entanglement.

The principles and operation of systems and methods according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Reference is now made to FIG. 1, which is an illustration of a vessel bifurcation with plaque buildup. A main vessel 1 and a branch vessel 2 meet at a bifurcation point 3. A buildup of plaque 4 may be found anywhere within the vessels, but if there is plaque buildup located at or close to bifurcation point 3, as shown in FIG. 1, the location presents a specific challenge with regard to accurate stent placement. Stents placed at bifurcations are typically deployed either slightly proximal or slightly distal to the bifurcation point, which can lead to stent jailing and/or insufficient coverage.

Reference is now made to FIG. 2, which is an illustration of a prior art bifurcation stent delivery system 5. System 5 includes a catheter 6 having a stent 7 with a dedicated side hole 8. A main guidewire 9 is positioned in main vessel 1 and passed through a main guidewire lumen in catheter 6. A side branch guidewire 11 is positioned within a second guidewire lumen, through side hole 8, and into branch vessel 2. As shown in FIG. 1, there is a tendency for system 5 to overshoot bifurcation point 3 during placement. Additionally, prior art bifurcation stent systems are generally large in diameter due to the presence of two guidewire lumens—one for main guidewire 9 and one for branch guidewire 11. Furthermore, the two wires often become entangled with one another, causing a failure in delivery and/or removal of the system.

The present invention seeks to address the limitations of prior art systems, by providing substantially predictable positioning and alignment, both translationally and rotationally within the vessel, while retaining a small profile and eliminating wire crossing so as to provide ease of delivery. Several different embodiments of the invention provide solutions for different types of lesions, as will be described in further detail hereinbelow.

Lesion Type 1, Type 2 and Type 4:

In a first embodiment, a stent delivery system 10 is designed to be delivered at a Type 1, Type 2 or Type 4 bifurcation lesion, as illustrated in FIGS. 29a, 29b and 29d, respectively. In these types of bifurcation lesions, the plaque 4 is at least partially located within the main vessel in the vicinity of bifurcation point 3, and may also be located within branch vessel 2.

Reference is now made to FIG. 3 and FIGS. 4a-d, which are illustrations of a bifurcation stent delivery system 10, shown with and without a stent respectively. System 10 includes a main elongated element 16, and an auxiliary elongated element 34 aligned with main elongated element 16. In a preferred embodiment, auxiliary elongated element 34 is positioned within main elongated element 16 proximal to an exit point 37 and alongside main elongated element 16 distal to exit point 37, as depicted in FIG. 3. In an alternative embodiment, auxiliary elongated element 34 is positioned alongside main elongated element 16, as will be described hereinbelow with reference to FIG. 8.

In a preferred embodiment, main elongated element 16 is a catheter 18 having a distal end 20 and a proximal end 22. A balloon 24 is positioned on distal end 20 of catheter 18. Catheter 18 includes a hypotube 25 running along a proximal portion of the catheter, and an inflation lumen within hypotube 25 in communication with balloon 24. Hyoptube 25 is comprised of stainless steel, or any other suitable material which provides rigidity. At a distal portion of catheter 18, a polymer jacket replaces hypotube 25, providing flexibility for navigation through the vessel. The inflation lumen continues to run through the polymer jacket portion of catheter 18 and into balloon 24. The inflation lumen is designed for introducing a fluid, preferably a liquid, into balloon 24 for inflation of balloon 24 at the appropriate location. A port for inflation is positioned at proximal end 22, in a configuration which is well known in the art. Catheter 18 shown in FIGS. 3 and 4a-d may be any commercially available balloon catheter. Optionally, a torquer device may be introduced to proximal end 22 for improving torqueability. Such torquer devices are well known in the art, and may be purchased, for example from Qosina Corp. (Edgewood, N.Y., USA, catalog part number 97333).

In an exemplary preferred embodiment, balloon 24 is a fixed wire balloon and as such, includes a fixed wire 26 attached to a distal end of balloon 24 at a bonding area 28. A core wire 30 (or skeleton) runs along the interior of balloon 24 to provide rigidity to the flexible portion of catheter 18. In a preferred embodiment, core wire 30 is a continuation of fixed wire 26. It is a particular feature of the present invention that core wire 30 is connected at a proximal end thereof to hypotube 25, at a distal end thereof to the distal end of balloon 24, and in at least one other location in between. Referring again to FIGS. 4a and 4c, core wire 30 is bonded to catheter 18 at an area of cross section B-B, where side branch lumen 36 exits catheter 18. Furthermore, core wire 30 is relatively thick as compared to a filament which is present within commercially available fixed wire balloons. Such filaments are typically within a range of 0.005 to 0.009 inches (most commonly around 0.007 inches), while the core wire 30 of the present invention is in a range of 0.009-0.012 inches (most preferably around 0.01 inches). This thickness, along with additional bonding of core wire 30 to catheter 18, provides rigidity along an entire length of catheter 18. This rigidity allows transmission of torque forces from proximal end 22 to distal end 20 of catheter 18, and minimal loss of such forces due to bending or twisting of the polymer jacket, thus providing enhanced torqueability of the system. Furthermore, the rigidity provided by core wire 30 and the features described above provide enhanced pushing capability of the system of the present invention, by preventing absorption of pushing forces by the polymer jacket or by other relatively compliant portions of system 10.

System 10 includes a stent 12 positioned on main elongated element 16, the stent 12 having a side opening 14. In one embodiment, side opening 14 is a dedicated side opening, and in another embodiment, side opening 14 is any opening within the structure of stent 12. For example, a stent having a diamond configuration of struts might not require a dedicated side opening, as any cell may be used to access the branch vessel. In a preferred embodiment, auxiliary elongated element 34 is a side branch lumen 36 for placement of a side branch guidewire therethrough. Side branch lumen 36 has a distal end 40 and a proximal end 42 and is attached to catheter 18 at proximal end 42 and unattached to catheter 18 at distal end 40. The point at which the detachment between main and auxiliary elongated elements (catheter 18 and side branch lumen 36 in the present embodiment) occurs is defined as a crotch point 44. In an alternative embodiment, side branch lumen 36 is unattached to catheter 18 both proximal and distal to crotch point 44, and is attached to catheter 18 only at crotch point 44. Core wire 30 further includes fluorescent markers 32 which can be visualized during a procedure under fluorescence. In a preferred embodiment, markers 32 are aligned with each end of stent 12 and with crotch point 44, forming a row of markers. In an exemplary preferred embodiment, an additional marker is included at distal end 40 of side branch lumen 36. This configuration provides a view of the rotational alignment of system 10 within the vessel. A discussion of marker configuration and alignment is discussed in more detail hereinbelow with respect to FIGS. 27a-d and 28. In alternative embodiments, any configuration of markers which would enable viewing of key locations of system 10 can be used.

Crotch point 44 is preferably located close to distal end 40 of side branch lumen 36. It should be noted that the depiction of crotch points in the figures is for indication purposes only, and that crotch points may not include an actual connecting element as shown. The length of the unattached portion is preferably less than 1 mm. In an exemplary preferred embodiment, the length of the unattached portion is approximately 0 mm, i.e. the distal end 40 of side branch lumen 36 is at crotch point 44. It should be noted that in this embodiment, a guidewire within side branch lumen 36 is configured to enter a side branch vessel, as will be described hereinbelow with reference to FIG. 5. This guidewire positioned within side branch lumen 36, and main elongated element 16 form crotch point 44. In an alternative embodiment, the length of the unattached portion is approximately 1-5 mm, or more preferably approximately 2 mm. Side branch lumen 36 may be as long or as short as necessary, both proximally and distally. In a preferred embodiment, the portion of side branch lumen 36 which is proximal to crotch point 44 is approximately 10-30 mm, and in an exemplary preferred embodiment is approximately 25 mm. By extending side branch lumen 36 proximally along at least a portion of hypotube 25, the rigidity of system 10 is increased, thus providing ease of rotation within the vessel. In an alternative embodiment, the portion of side branch lumen 36 which is proximal to crotch point 44 is approximately 5-15 mm.

Cross-sectional views along lines A-A, B-B and C-C are depicted in FIGS. 4b, 4c and 4d, respectively. As shown in FIG. 4b, at a proximal location, side branch lumen 36 is located within catheter 18. Core wire 30 is in the center, and side branch lumen 36 is between core wire 30 and the edge of catheter 18. As shown in FIG. 4c, at exit point 37, side branch lumen 36 is bonded to catheter 18. Distal to exit point 37, side branch lumen 36 is outside and adjacent to balloon 24, as shown in FIG. 4d.

Reference is now made to FIG. 5, which is an illustration of system 10 positioned at a bifurcation. Crotch point 44 is a key element in positioning of stent 12 within the vessel. With catheter 18 in main vessel 1 and a side branch guidewire 38 within side branch lumen 36 positioned in branch vessel 2, system 10 cannot be advanced beyond the point at which crotch point 44 reaches bifurcation point 3. Thus, system 10 is substantially predictably aligned, and overshooting is prevented. Side branch guidewire 38 is chosen to have optimal stiffness. In a preferred embodiment, guidewire 38 has an intermediate stiffness, such that it is stiff enough to guide system 10 and to prevent system 10 from advancing beyond crotch point 44, but not too stiff so as to risk puncturing the vessel.

In an exemplary preferred embodiment, a method for introducing system 10 is as follows. First, a side branch guidewire 38 is positioned within branch vessel 2. A proximal end of side branch guidewire 38 is introduced into distal end 40 of side branch lumen 36. With side branch guidewire 38 positioned within side branch lumen 36, system 10 is advanced through main vessel 1. Fixed wire 26 provides guidance as advancement occurs. In an alternative embodiment, side branch guidewire 38 is not introduced initially, and system 10 is advanced using only fixed wire 26 as a guide. In this embodiment, side branch guidewire 38 is initially backloaded into side branch lumen 36 and remains within side branch lumen 36 as system 10 is advanced through main vessel 1. In either case, system 10 is free to rotate without risk of entanglement. When crotch point 44 reaches bifurcation point 3, advancement of system 10 automatically stops. At this point, system 10 is in place, with side branch guidewire 38 in branch vessel 2, and stent 12 in a correct position both translationally and rotationally. Balloon 24 is then inflated, thus deploying stent 12 within the vessel. Thus, the exact location of crotch point 44 predetermines accuracy of positioning. After deployment, system 10 is removed from branch vessel 2. A particular feature of the invention as described is the ability to provide rapid exchange of catheters via branch guidewire 38, if necessary.

It should be apparent that the specific features of the present invention allow for accurate positioning in both the rotational and the translational direction, while providing a small outer diameter overall. In a preferred embodiment, the overall outer diameter is 0.5-1.5 mm. Specifically, by attaching side branch lumen 36 directly to balloon 24, for example, and predetermining the location of crotch point 44, side branch lumen 36 acts as a guide in the translational plane. The use of a fixed wire provides torqueability and ease of rotation, particularly since there is only one guidewire present (i.e. the branch guidewire). The presence of a bonded, relatively thick core wire 30 provides rigidity and ease of transmission of torque and pushing forces. The configuration of side branch lumen 36 wherein a distal end 40 thereof is unattached to main elongated element 16, or wherein a guidewire placed therethrough is unattached to main elongated element 16 allows for initial entry of side branch lumen 36 into branch vessel 2. These aspects allow for substantially predictable rotation of the system and substantially predictable rotational positioning, without wire entanglement.

In one embodiment, the system 10 illustrated in FIGS. 3, 4a-d and 5 is configured for use in treating an intracranial aneurysm. Current methods for treating such aneurysms include the use of self-expanding stents such as, for example, the Neuroform™ stents manufactured by Boston Scientific Corp. (MA, USA). Specifically, such stents are presented to the site of the aneurysm and deployed, after which a standard microcatheter is introducible through openings of the deployed stent. An embolic coil is introduced into the aneurysm through the microcatheter to plug the site of the aneurysm. Self expanding stents are generally used due to their low profile and maneuverability, features which are crucial for small vessels associated with intracranial aneurysms. However, they are prone to positioning problems and are difficult to anchor in place during deployment. A system such as the one described in preferred embodiments of the present invention can be used in place of self expanding stents for treatment of aneurysms, and provide both the benefits of small profile and maneuverability as well as better positioning and anchoring.

Figure 30A:
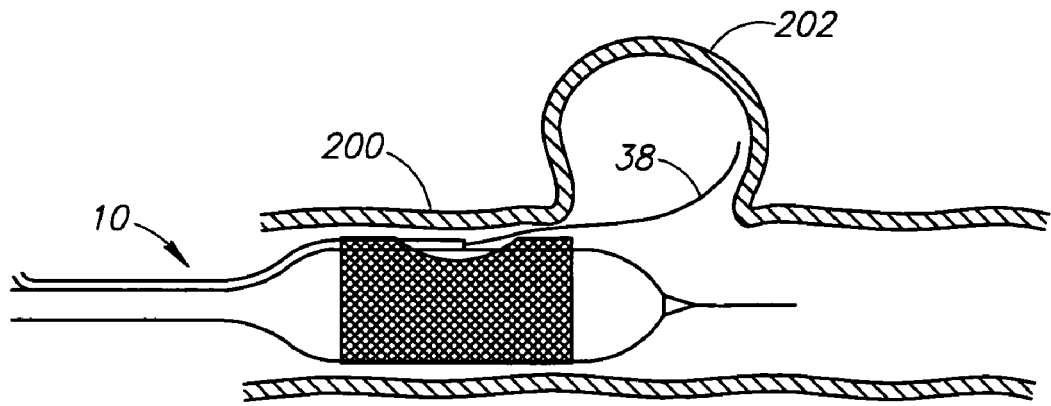
FIGS. 30A-30E are illustrations of steps of a method of treating an intracranial aneurysm, in accordance with embodiments of the present invention.
Figure 30B:
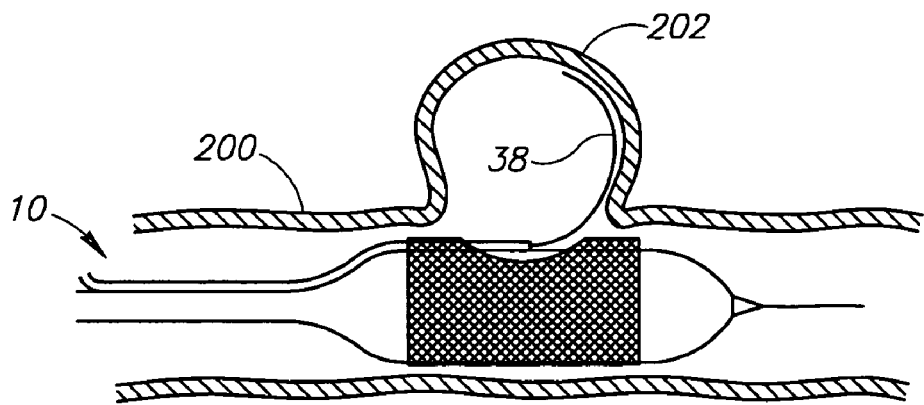
Figure 30C:
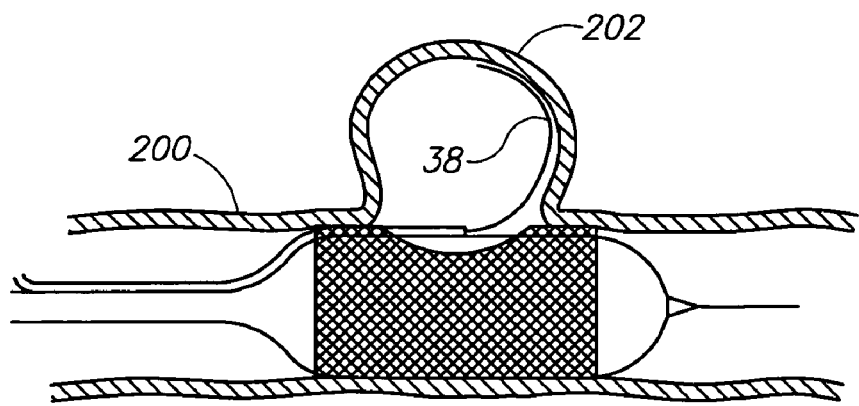
Figure 30D:
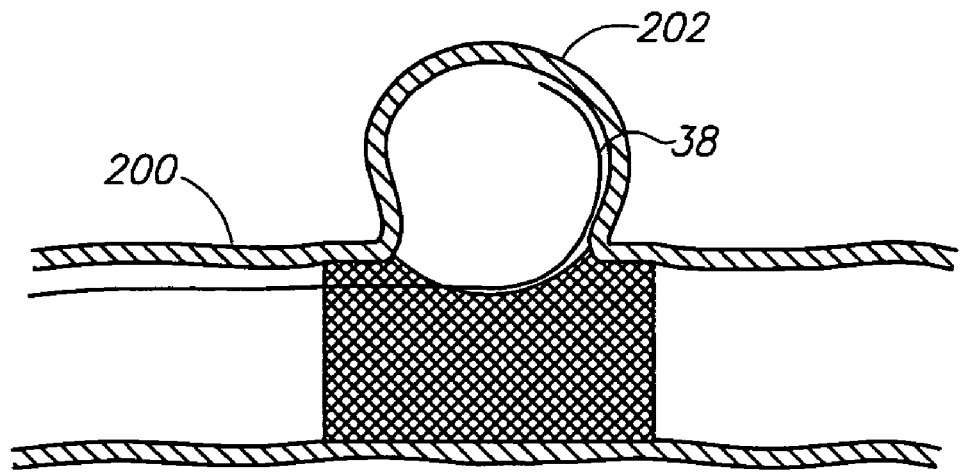
Figure 30E:
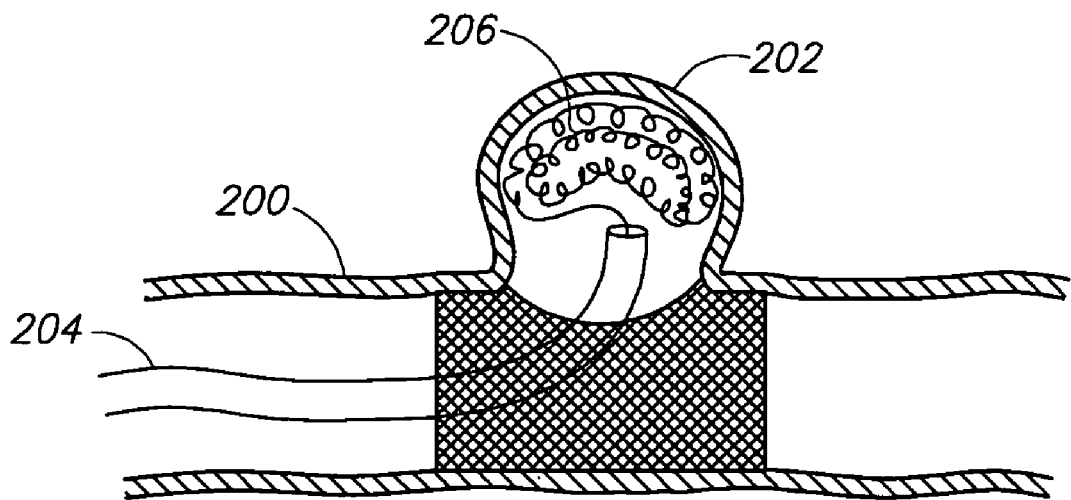

Reference is now made to FIGS. 30A-30E, which are illustrations of steps of a method for treating an intracranial aneurysm in accordance with one embodiment of the present invention. As shown in FIG. 30A, system 10 is introduced into a vessel 200 with an aneurysm 202, and positioned such that side opening 14 of stent 12 is situated at the site of the aneurysm, as shown in FIG. 30B. Alternatively, a stent without a side opening may be used. Positioning may be done by using markers and/or by the introduction of guidewire 38 through side branch lumen 36. Once the system is in place, stent 12 is deployed, as shown in FIG. 30C. Catheter 18 is removed, leaving stent 12 and guidewire 38 in place at the site of the aneurysm, as shown in FIG. 30D. As shown in FIG. 30E, a standard microcatheter 204 is then introduced over guidewire 38 through side opening 14 and into the area of the aneurysm, through which an embolic coil 206 may be delivered to the site.

Reference is now made to FIG. 6, which is an illustration of system 10 in accordance with an alternative embodiment of the present invention. As shown in FIG. 6, system 10 further includes a distal connecting element 46, attached to a distal end of balloon 24. In a preferred embodiment, distal connecting element 46 is attached at bonding area 28 of balloon 24. In an alternative embodiment, distal connecting element 46 is attached at any other location on balloon 24 which is distal to side branch lumen 36. Distal connecting element 46 is configured to hold side branch guidewire 38 in place until system 10 is in the vicinity of bifurcation 3. This prevents side branch guidewire 38 from moving around within the vessel during delivery of system 10, possibly causing damage. Once system 10 is within the general vicinity of bifurcation 3, side branch guidewire 38 is pulled proximally and released from distal connecting element 46, after which it is advanced into branch vessel 2. System 10 is then advanced until crotch point 44 prevents further advancement, balloon 24 is inflated, and stent 12 is deployed.

Reference is now made to FIG. 7, which is an illustration of system 10 in accordance with yet another embodiment of the present invention. As shown in FIG. 7, side branch lumen 36 is located internally within balloon 24, and includes an exit point 37 at a location along balloon 24. The location of exit point 37 with respect to stent 12 defines a crotch point, which coincides with the location of crotch point 44 described in the earlier embodiments, and is functionally equivalent thereto. In one embodiment, side branch lumen 36 ends at crotch point 44. In an alternative embodiment, side branch lumen 36 extends distally beyond crotch point 44.

Reference is now made to FIG. 8, which is an illustration of system 10 in accordance with yet another embodiment of the present invention. Side branch lumen 36 is located external and adjacent to main elongated element 16. Crotch point 44 is located distal to an attachment point between side branch lumen 36 and balloon 24. The portion of side branch lumen 36 which lies between the attachment point and crotch point 44 may be attached or unattached to balloon 24.

Reference is now made to FIGS. 9a and 9b, which are illustrations of system 10 in accordance with yet another embodiment of the present invention, shown with a stent thereon. In this depiction, side hole 14 is not a dedicated side hole, but rather is any opening within the body of stent 12. It should be noted that this type of stent may be included on any of the embodiments described herein. System 10 includes a main guidewire 39 rather than a fixed wire at the distal end of balloon 24. A main guidewire lumen 50 is located at bonding area 28 of balloon 24. In a preferred embodiment, main guidewire lumen 50 is relatively short, i.e. 1-5 mm. In alternative embodiments, main guidewire lumen 50 extends proximally along a side of balloon 24. In a preferred embodiment, main guidewire 39 is positioned outside of stent 12 so as to avoid wire crossing between main guidewire 39 and side branch guidewire 38, as shown in FIG. 9a. In an alternative embodiment, main guidewire 39 is positioned within stent 12, as shown in FIG. 9b. In a preferred embodiment, main guidewire lumen 50 is positioned on an opposite side from side branch lumen 36, as depicted.

In an alternative embodiment (not shown) of the present invention, system 10 includes a main guidewire lumen in place of a fixed wire, and further includes a crotch point 44 in accordance with the different embodiments described above.

Figures 31A, 31B:
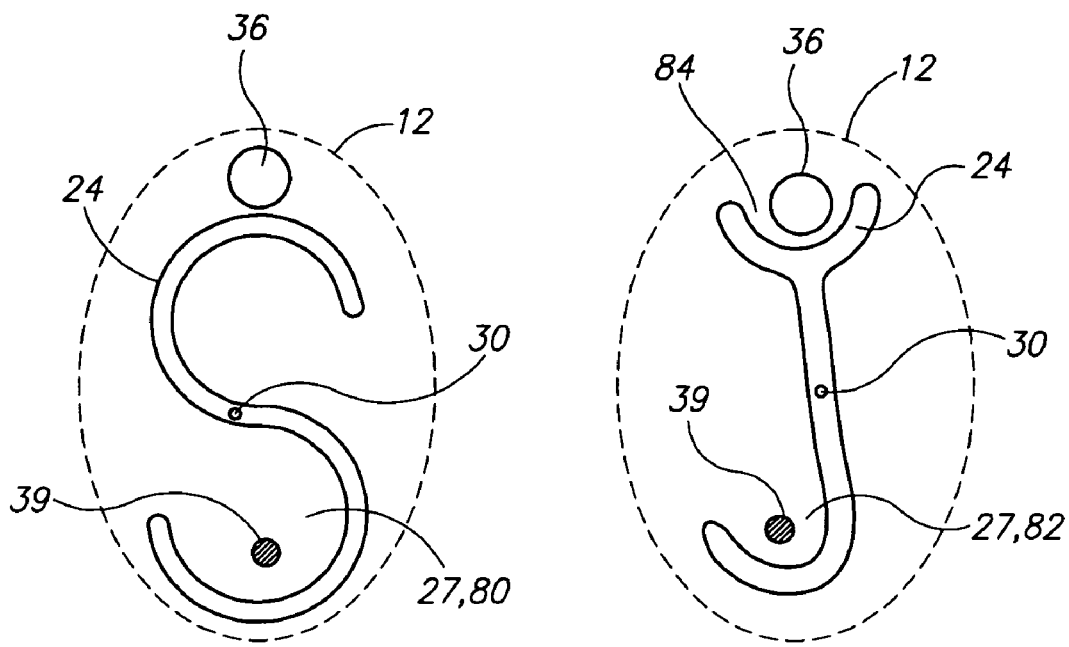
FIGS. 31A and 31B are cross-sectional illustrations of a balloon in its deflated state and having a guidewire positioned within a temporary lumen, in accordance with embodiments of the present invention.

The embodiment shown in FIG. 9b allows for main guidewire 39 to be fixed during insertion and movable after inflation of balloon 24. In one embodiment, main guidewire 39 is fixed during insertion by crimping of a stent thereon. In another embodiment, balloon 24 is formed to hold guidewire 39 therein prior to inflation and to release guidewire 39 following inflation. The configuration of balloon 24 forms a "temporary lumen", defined as a lumen which is present on balloon 24 only in a deflated state. That is, inflation of balloon 24 causes balloon 24 to unfold, resulting in a disappearance of the temporary lumen and release of guidewire 39. Reference is now made to FIGS. 31a and 31b, which are cross-sectional illustrations of system 10 showing balloon 24 in a deflated state with main guidewire 39 positioned within a temporary lumen 27, in accordance with embodiments of the present invention. As shown in FIG. 31A, balloon 24 is folded in an "S" shape having a containment area 80 in one of the curved portions of the "S" shape. Main guidewire 39 is positioned in containment area 80, while auxiliary elongated element 34 is positioned outside of balloon 24. Stent 12 is positioned around balloon 24, main guidewire 39 and auxiliary side branch lumen 36. In another embodiment, shown in FIG. 31B, balloon 24 is folded in a hooked "Y" shape, wherein the bottom portion of the "Y" shape is curved to form a containment area 82. The portion of the "Y" shape determined by the two arms of the "Y" acts as a secondary containment area 84 for holding side branch lumen 36 therein. Containment area 80 or 82 acts as a temporary lumen 27, at least partially containing main guidewire 39 therein until inflation of balloon 24. Stent 12 is positioned around balloon 24, main guidewire 39 and side branch lumen 36.

In this embodiment, side branch lumen 36 is a guidewire enclosure for placing of a guidewire therethrough. In a preferred embodiment the guidewire enclosure is at least partially attached to the catheter at the crotch point. In a preferred embodiment, the guidewire enclosure is at least partially positioned within the catheter body so as to minimize the outer profile of the catheter. The distal end of the guidewire enclosure can be located at or distal to the attachment point.

In a preferred embodiment, a guidewire lumen 50 is attached to the balloon distal end, and has a length of less than 15 mm. The containment area 80 or 82 forming temporary lumen 27 is preferably longitudinally aligned with the guidewire lumen, such that a distal end of the guidewire is positionable through the guidewire lumen and a portion of the guidewire which is proximal to the distal end of the guidewire is positionable in the temporary lumen 27. In a preferred embodiment, the temporary lumen 27 and the guidewire lumen are on an opposite side from the guidewire enclosure. According to additional features, the guidewire enclosure is at least partially positioned within said catheter body and is attached to the catheter body at a location on the balloon. The location is approximately in a center of the balloon.

During a procedure, the catheter system with guidewire 39 positioned through guidewire lumen 50 and in temporary lumen 27 is introduced into the vessel. Upon inflation of the balloon, guidewire 39 is released from temporary lumen 27, and becomes movable with respect to the catheter. In a preferred embodiment, a housing positioned proximal to a proximal end of temporary lumen 27 holds a portion of guidewire 39 in place. Furthermore, a torquer may be placed at a proximal end of the catheter. The method provides the benefits of a fixed wire, with the additional benefit of a second guidewire positioned in the vessel during the procedure.

Lesion Types 4A and 4B:

In a second embodiment, a stent delivery system 110 is designed to be delivered at a Type 4A or 4B bifurcation lesion as illustrated in FIGS. 29e and 29f. In a Type 4A lesion, plaque 4 is located in branch vessel 2, at or near bifurcation 3. In a Type 4B lesion, plaque 4 is located in main vessel 1 distal to the point of bifurcation 3. One example of such a location is the coronary artery, where blockage of, for example, the left anterior descending (LAD) artery is to be avoided while providing coverage to the plaque within the coronary artery. Other examples include renal arteries, the left main coronary artery, vein grafts, and others.

Figure 11B:
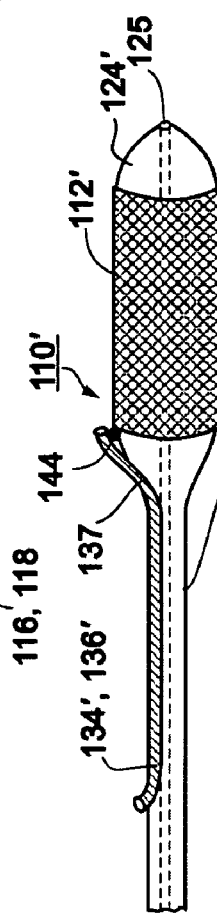
Figure 11C:
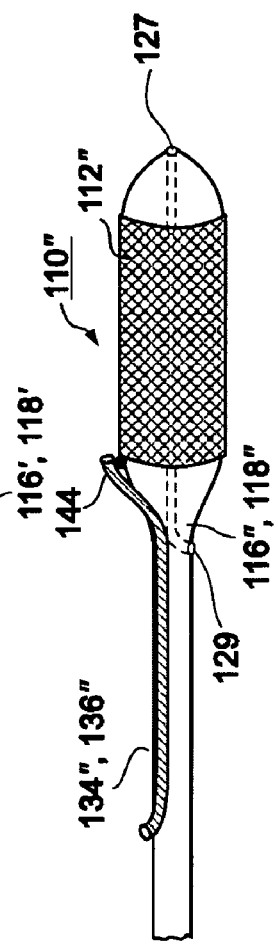

Reference is now made to FIGS. 11a-c, which are illustrations of different embodiments of a system 110 for delivery of a stent at a Type 4A or Type 4B bifurcation lesion. System 110 may be designed with a fixed wire, as shown in FIG. 11a, as on over-the-wire system, as shown in FIG. 11b, or as a rapid exchange system, as shown in FIG. 11c.

Reference is now made to FIG. 11a, which is an illustration of system 110 designed as a single wire system. System 110 includes a main elongated element 116 and an auxiliary elongated element 134. In a preferred embodiment, main elongated element 116 is a catheter 118. In a preferred embodiment, catheter 118 includes a balloon 124 with a fixed wire 126 at a distal end thereof. A stent 112 is positioned on balloon 124. In a preferred embodiment, auxiliary elongated element 134 is a side branch lumen 136, and is attached to catheter 118 at a crotch point 144. Side branch lumen 136 has a proximal end 142 and a distal end 140. In a preferred embodiment, side branch lumen 136 is positioned within catheter 118 proximally, exits at an exit point 137, and is attached to main elongated element 116 at crotch point 144. The portion of side branch lumen 136 between exit point 137 and crotch point 144 may be attached or unattached. In a preferred embodiment, a distal end of side branch lumen 136 is at crotch point 144, and a guidewire placed therethrough extends distally to provide a stopping point. In an alternative embodiment, the distal end of side branch lumen is located 1-5 mm distal to crotch point 144, and is unattached to the catheter 118 in this location.

In an alternative embodiment, side branch lumen 136 is located external to and positioned alongside catheter 118 proximal to crotch point 144, and is unattached to elongated element 116 distal to crotch point 144. In an alternative embodiment, side branch lumen 136 is unattached to catheter 118 both proximal to and distal to crotch point 144. Crotch point 144 is located at or near a proximal end of stent 112. In a preferred embodiment, crotch point 144 is just proximal to the proximal end of stent 112.

Reference is now made to FIG. 11b, which is an illustration of system 110' designed as an over-the-wire, double rail system. System 110' is similar to system 110 shown in FIG. 11a, except that in place of a fixed wire on the distal end of balloon 124', a main guidewire lumen 125 is present and runs the length of catheter 118'. A main guidewire is positioned through main guidewire lumen 125 for entry into main vessel 1. System 110' may be introduced to the site via a main guidewire located in main guidewire lumen 125 or via a branch guidewire located in side branch lumen 136'.

Reference is now made to FIG. 11c, which is an illustration of system 110", designed as a rapid exchange dual wire system. System 110" is similar to both systems 110 and 110' depicted in FIGS. 11a and 11c, except that in place of a fixed wire or a main guidewire lumen running the length of catheter 118", a short main guidewire lumen 127 is present and runs proximally until an exit point 129. These types of systems are well known in the art, and are known to provide ease of catheter exchange. In the present invention, the location of crotch point 144 allows for more accurate placement within the vessel.

Figure 12:
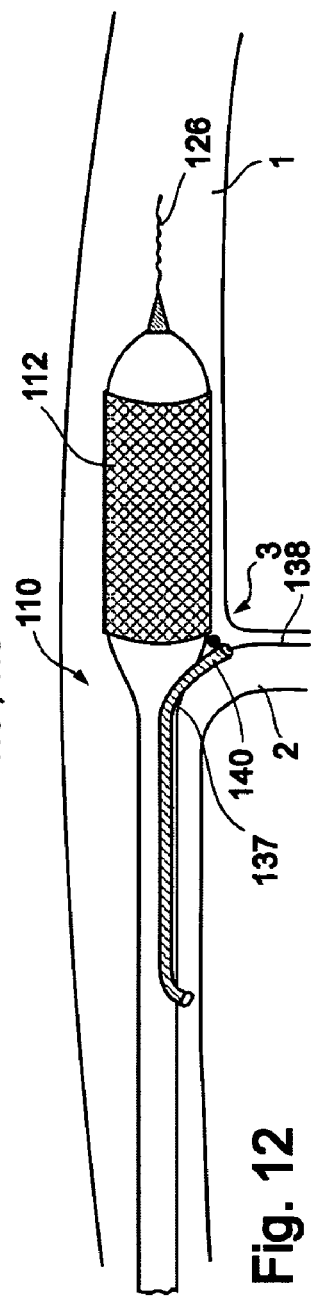
FIG. 12 is an illustration of the system of FIG. 11a in position at a bifurcation.

Reference is now made to FIG. 12, which is a depiction of system 110 positioned at bifurcation 3 for a Type 4B lesion. A side branch guidewire 138 is introduced into branch vessel 2. System 110 is guided over side branch guidewire 138 and either fixed wire 126 or a main guidewire 139, depending on the type of system, until crotch point 144 of side branch lumen 136 is at bifurcation point 3. In a preferred embodiment, distal end 140 is at crotch point 144, and only guidewire 138 enters branch vessel 2. In an alternative embodiment, side branch lumen 136 extends and into side branch vessel 2. System 110 is slowly advanced until crotch point 144 reaches bifurcation point 3, after which system 110 automatically stops advancing. Balloon 124 is then inflated, deploying stent 112. After deployment, balloon 124 is deflated, and system 110 is removed. For a Type 4A lesion, a similar method would be used, but side branch guidewire 138 would be introduced into main vessel 3, and system 110 would be guided into branch vessel 2.

Figure 32:
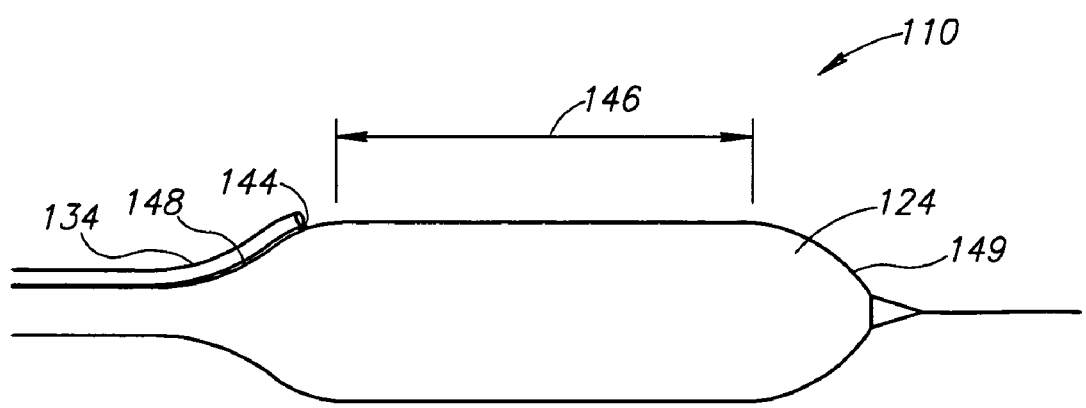
FIG. 32 is an illustration of a system without a stent, in accordance with embodiments of the present invention.

In an alternative embodiment, system 110 is a catheter system and does not include a stent, as shown in FIG. 32. Crotch point 144 is an attachment point which is located at or near a proximal end of balloon 124, rather than at or near a proximal end of stent 112. More specifically, balloon 124 includes a working length portion 146, a proximal narrowed portion 148, and a distal narrowed portion 149. Working length portion 146 is defined as the portion of balloon 124 with the largest outer diameter, while proximal and distal narrowed portions 148, 149 are the portions of balloon 124 which have a smaller diameter than working length portion 146. In one embodiment, crotch point 144 is proximal to working length portion 146, and in some embodiments is located at a junction where working length portion 146 meets up with proximal narrowed portion 148. Auxiliary elongated element 134 is a guidewire enclosure for placing of a guidewire therethrough. In a preferred embodiment the guidewire enclosure is at least partially attached to the catheter at the crotch point. In a preferred embodiment, the guidewire enclosure is at least partially positioned within the catheter body so as to minimize the outer profile of the catheter. The distal end of the guidewire enclosure can be located at or distal to the attachment point.

A catheter system having a fixed wire balloon and a partially attached guidewire enclosure such as described above may be beneficial in treating both regular lesions and bifurcated lesions. For a non-bifurcated lesion, a guidewire is introduced into the vessel and through the lesion. The catheter is then advanced over the guidewire by introducing a proximal end of the guidewire into the guidewire enclosure of the catheter. The catheter is advanced until it reaches the lesion, and is thus in a position such that the guidewire lies alongside the balloon. Upon inflation of the balloon, the guidewire is compressed into the lesion site, and provides a focused force to enable the user to crack hard lesions at low pressure before the balloon is fully inflated. Doing so allows vessel stretching to occur at a lower strain rate, thus minimizing the trauma associated with balloon dilatation.

The presence of a guidewire enclosure further provides an opportunity to treat lesions located at a bifurcation without reintroduction of the system. After treatment of a lesion in the first vessel, a second vessel which is connected to the first vessel at a bifurcation can be treated using the same guidewire. After treatment of the first lesion, the balloon is deflated, the catheter is retracted along the guidewire, and introduced into the second vessel. The balloon is then inflated so as to compress the lesion in the second vessel.

In an alternative method, the guidewire is introduced into the second vessel, the catheter is advanced over the guidewire past the bifurcation and into the first vessel. The first lesion is then treated by inflating the balloon and compressing the lesion. The balloon is deflated, the catheter is retracted, and introduced into the second vessel such that the guidewire is positioned alongside the balloon. Upon inflation of the balloon, the guidewire is compressed into the lesion site, and provides a focused force to enable the user to crack hard lesions at low pressure before the balloon is fully inflated.

In an alternative embodiment, a stent delivery system 210 is designed to be delivered at a bifurcation lesion such as the one illustrated in FIG. 13, having a main vessel 1 and a branch vessel 2 at an angle with respect to main vessel 1, and wherein plaque 4 is located in branch vessel 2 at an area of a bifurcation 3. In an exemplary preferred embodiment, main vessel 1 is an aorta.

Reference is now made to FIGS. 14a and 14b, which are views of a system 210 in accordance with an embodiment of the present invention. System 210 includes a main elongated element 216 and an auxiliary elongated element 234. In a preferred embodiment, main elongated element 216 is a catheter 218 having a proximal end 222 and a distal end 220. Catheter 218 has a balloon 224 at distal end 220, with a stent 212 positioned thereon. In one embodiment, balloon 224 includes a main guidewire lumen 227. In an alternative embodiment, balloon 224 is a fixed wire balloon, such as described with reference to the first and second embodiments, and shown at least in FIGS. 4a and 11a. In a preferred embodiment, main guidewire lumen 227 extends only partially in the proximal direction along catheter 218 and includes an exit point 229 for rapid exchange. In an alternative embodiment, system 210 is an over-the-wire system and main guidewire lumen 227 extends proximally to the proximal end of catheter 218. In a preferred embodiment, auxiliary elongated element 234 is a positioning system 236, which will be described in further detail hereinbelow.

In a preferred embodiment, positioning system 236 includes a stopper element 250 and an attachment mechanism 252. In a preferred embodiment, stopper element 250 is separate from attachment mechanism 252 and comprises, for example, spring wires, flexible polymers, or any other material which can be extended in a first configuration and which can be folded, sprung or otherwise positioned to act as a stopper in a second configuration. In an alternative embodiment, stopper element 250 is part of attachment mechanism 252, but can also be extended in a first configuration and positioned to act as a stopper in a second configuration. In one preferred embodiment, stopper element 250 is comprised of a shape memory metal such as, for example, Nitinol. In the embodiment described herein, spring wires are used as stopper element 250, which are designed to lay substantially horizontal to catheter 218 in their unextended positions and to coil or spring into a stopper upon release. Attachment mechanism 252 attaches the spring wires to main elongated element 216 to form crotch points 244. In a preferred embodiment, attachment mechanism 252 is a jacket having a proximal end 256 and a distal end 254. Attachment mechanism 252 at least partially encloses stopper element 250 (shown as spring wires), such that a proximal portion of stopper element 250 enclosed by attachment mechanism 252 is relatively straight, and a distal portion of stopper element 250 is unenclosed and able to move freely. Attachment mechanism 252 can comprise any biocompatible material, and is preferably comprised of a polymer. In a preferred embodiment, crotch points 244 are located at a proximal end of balloon 224.

Reference is now made to FIG. 14*b*, which is a cross-sectional view of system 210 along the lines A-A, in accordance with one embodiment. Catheter 218 has main guidewire lumen 227 for introduction of a main guidewire 239. Surrounding catheter 218 is stopper element 250, which is held in place by attachment mechanism 252.

Reference is now made to FIGS. 15*a-b*, which are illustrations of system 210 partially enclosed within a holder 254. The purpose of holder 254 is to temporarily hold stopper element 250 in a substantially straight configuration until the area of bifurcation point 3 is reached. In a preferred embodiment, holder 254 is a peel-away device. When holder 254 is in place, stopper element 250 is enclosed and lies approximately along the plane of main elongated element 216. In the embodiment shown in FIGS. 15*a* and *b*, stopper elements 250 are straightened in the distal direction, such that they run alongside stent 212. The area proximal to crotch points 244 is shown in cross section in FIG. 15*b*, and includes a main guidewire lumen 227 within catheter 218, stopper elements 250 enclosed within attachment mechanism 252, and holder 254 surrounding attachment mechanism 252.

Reference is now made to FIGS. 16*a-b*, which are illustrations of system 210 partially enclosed within holder 254, in accordance with another embodiment of the present invention. In the illustration shown in FIGS. 16*a* and *b*, stopper elements 250 are bent in a proximal direction, with holder 254 surrounding stopper elements 250 and holding them in place. That is, stopper elements 250 are folded over attachment mechanism 252. The area proximal to crotch points 244 is shown in cross section in FIG. 16*b*, and includes a main guidewire lumen 227 within catheter 218, stopper elements 250 enclosed both within and outside of attachment mechanism 252, and holder 254 surrounding attachment mechanism 252 and stopper elements 250.

Reference is now made to FIG. 17, which is a depiction of system 210 within a guiding catheter 260. Guiding catheter 260 includes a proximal end 262, through which system 210 is introduced, and a distal end 264, which is open to a vessel. As system 210 is guided into proximal end 262 of guiding catheter 260, holder 254 is removed, since stopper element 250 will remain in place within guiding catheter 260. In a preferred embodiment, holder 254 is a peel-away system, wherein the outer walls may be peeled away and removed from the system while system 210 is being introduced into guiding catheter 260. This introduction is performed outside of the body. In an alternative embodiment, holder 254 is a sheath, which can be pulled back as system 210 is being introduced into guiding catheter 260. Holder 254 can be any device for holding stopper element 250 in place until system 210 is within guiding catheter 260.

Reference is now made to FIGS. 18*a* and 18*b*, which are depictions of a method for introducing system 210 to a bifurcation in accordance with an embodiment of the present invention. Guiding catheter 260 with system 210 positioned therein is introduced through main vessel 1 until bifurcation point 3. Distal end 264 of guiding catheter 260 is visualized using methods currently known in the art, such as, for example, fluorescent markers. Once distal end 264 of guiding catheter 260 is at the entrance to branch vessel 2, system 210 is advanced through distal end 264 of guiding catheter 260, as shown in FIG. 18*a*. As system 210 is advanced, stopper elements 250 are no longer held in place by guiding catheter 260, and will spring or coil into their second configuration, acting as stoppers, as shown in FIG. 18*b*. System 210 is then advanced until stopper elements 250 prevent system 210 from further advancement, as shown in FIG. 18*c*. At this point, system 210 is properly positioned, and stent 212 is deployed.

Y-Bifurcation:

In another embodiment, a stent delivery system 310 is designed to be delivered at a bifurcation 3 as illustrated in FIG. 19, having a Y-configuration. Main vessel 1 branches into two branch vessels: a first branch vessel 2 and a second branch vessel 2', and plaque 4 is located in main and/or branch vessels at the area of bifurcation point 3.

Reference is now made to FIG. 20, which is an illustration of a stent delivery system 310, in accordance with one embodiment of the present invention. System 310 includes a main elongated element 316 and an auxiliary elongated element 334. In a preferred embodiment, main elongated element 316 is a catheter 318. Catheter 318 has a proximal end 322 and a distal end 320. Proximal end 322 includes a hub 321 having a Y-valve for dual inflation. Distal end 320 has two balloons: a proximal balloon 324 and a distal balloon 325. Each of proximal and distal balloons 324 and 325 is in fluid communication with its own inflation channel. An outer inflation channel 335 communicates with proximal balloon 324 and an inner inflation channel 327 communicates with distal balloon 325. Outer inflation channel 335 is coaxial with inner inflation channel 327. Alternatively, outer inflation channel 335 and inner inflation channel 327 are positioned side by side. In either case, balloons 324 and 325 may be inflated separately. In an alternative embodiment, outer inflation channel communicates with distal balloon 325 and inner inflation channel 327 communicates with proximal balloon 324. In a preferred embodiment, distal balloon 325 has a fixed wire 326 at a distal end thereof. In alternative embodiments, system 310 includes a main guidewire lumen or a short external guidewire lumen such as distal connecting element 50 shown in FIG. 6.

In a preferred embodiment, auxiliary elongated element 334 is a side branch lumen 336 having a proximal end 342 and a distal end 340. In a preferred embodiment, side branch lumen 336 is located internally within catheter 318, and exits therefrom at an exit point 337. Distal to exit point 337, side branch lumen 336 is adjacent to proximal balloon 324 and attached thereto at a crotch point 344. In an alternative embodiment, side branch lumen 336 lies alongside proximal balloon 324.

Reference is now made to FIG. 21, which is an illustration of system 310 with stents. In a preferred embodiment, two stents are included, as shown. A proximal stent 312 is positioned on proximal balloon 324, and a distal stent 313 is positioned on distal balloon 325. Each stent may be separately deployed by inflating its corresponding balloon. Proximal stent 312 is positioned such that distal end of side branch lumen 336 is approximately aligned with a distal end of proximal stent 312. The distal edges of side branch lumen 336 and stent 312 form a crotch point 344. In an alternative embodiment, side branch lumen 336 extends distally past crotch point 344. All of the embodiments described earlier in the present application may further be applied here.

In alternative embodiments, system 310 includes one, two or no stents, depending on the application. For example, system 310 may be used for predilatation, with a stent only on proximal balloon 324. Alternatively, a tapered vessel may require two different stent sizes, wherein one stent of a particular size is positioned on distal balloon 325, while another stent of a different size is positioned on proximal balloon 324.

Figure 22A:
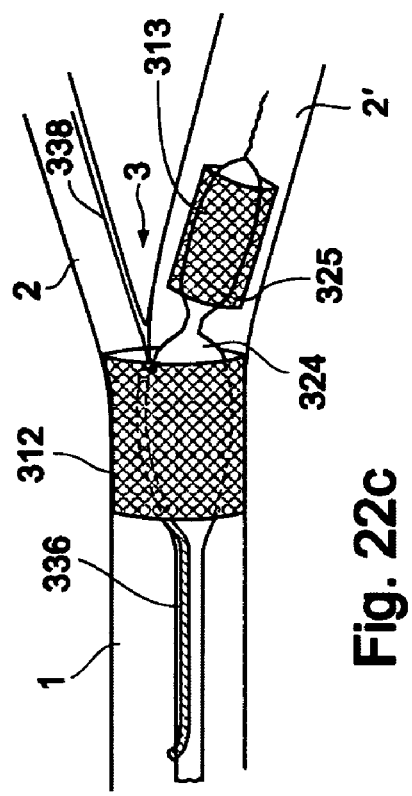
FIGS. 22a-d are illustrations of a method of deploying the system of FIG. 20.
Figure 22B:
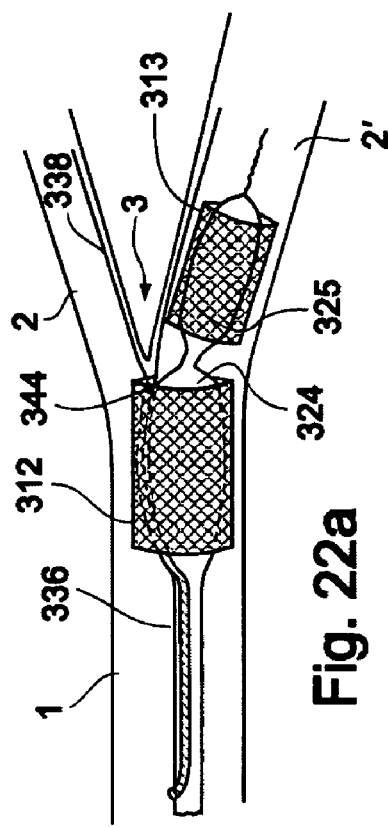
Figure 22C:
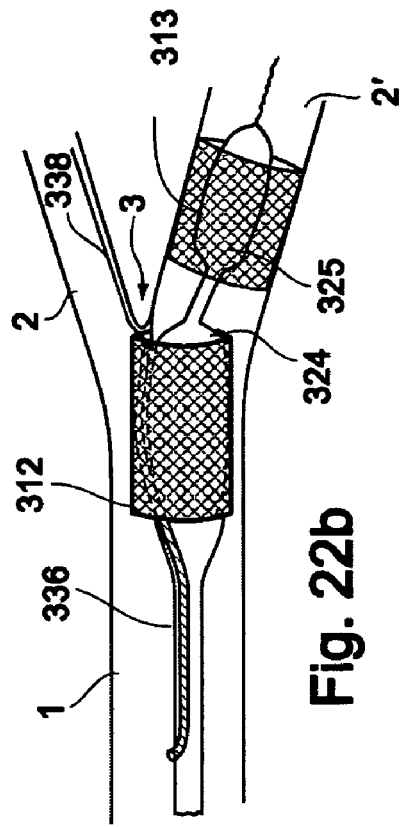
Figure 22D:
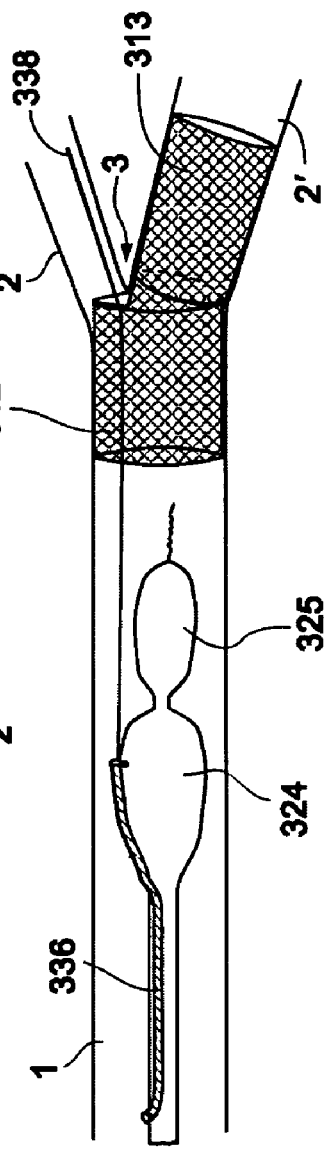

Reference is now made to FIGS. 22a-d, which are illustrations of a method of deploying system 310 within a Y-bifurcation. First, a side branch guidewire 338 is introduced into a first branch vessel 2. A proximal end of side branch guidewire 338 is then placed through a distal end of side branch lumen 336. System 310 is advanced over side branch guidewire 38 through main vessel 1 and into second branch vessel 2'. When crotch point 344 reaches bifurcation 3, system 310 will not be advanceable, and system 310 will be in place, as shown in FIG. 22a. As shown in FIG. 22b, distal balloon 325 is inflated via inner inflation channel 327, deploying distal stent 313 in a branch vessel, just distal to bifurcation point 3. After deployment of distal stent 313, proximal balloon 324 is inflated via outer inflation channel 335, deploying proximal stent 312. An alternate method is depicted in FIG. 22c, wherein proximal stent 312 is deployed first, and then distal stent 313 is deployed. In an alternative embodiment, both stents are deployed simultaneously. The final result with both stents deployed and in position is shown in FIG. 22d.

Reference is now made to FIG. 23, which is an illustration of a tapered balloon system 410, in accordance with an alternative embodiment of the present invention. Similar to the earlier embodiments, tapered balloon system 410 includes a main elongated portion and an auxiliary elongated element 434. In a preferred embodiment, auxiliary elongated element 434 is a side branch lumen. A balloon has a proximal outer diameter and a distal outer diameter which is different from the proximal outer diameter. In a preferred embodiment, the distal outer diameter is smaller than the proximal outer diameter, although the reverse may be provided as well. This type of balloon system may be useful for introduction of a tapered stent into a vessel, so as to avoid over-expansion of a stent within a distal portion of the vessel.

Lesion Type 3:

In another embodiment, a stent delivery system 510 is designed to be delivered at a Type 3 bifurcation lesion as illustrated in FIG. 29c. In a Type 3 lesion, plaque 4 is located in main vessel 1, proximal to the point of bifurcation 3. Stent delivery system 510 is also suitable to be delivered at a lesion in a non-bifurcated vessel, as will be described more fully hereinbelow.

Figure 24A:
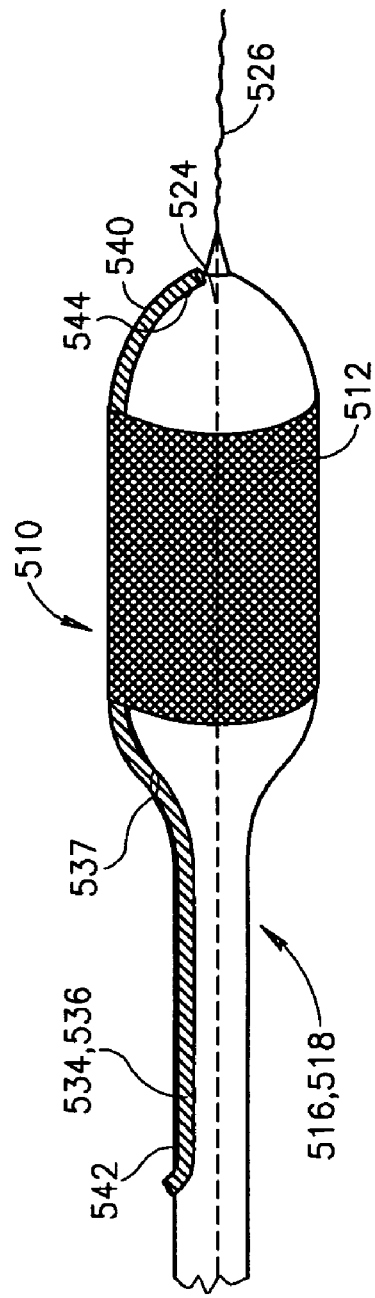
FIGS. 24a-c are illustrations of different embodiments of a system for delivery of a stent at a Type 3 bifurcation lesion or at a non-bifurcated lesion.
Figure 24B:
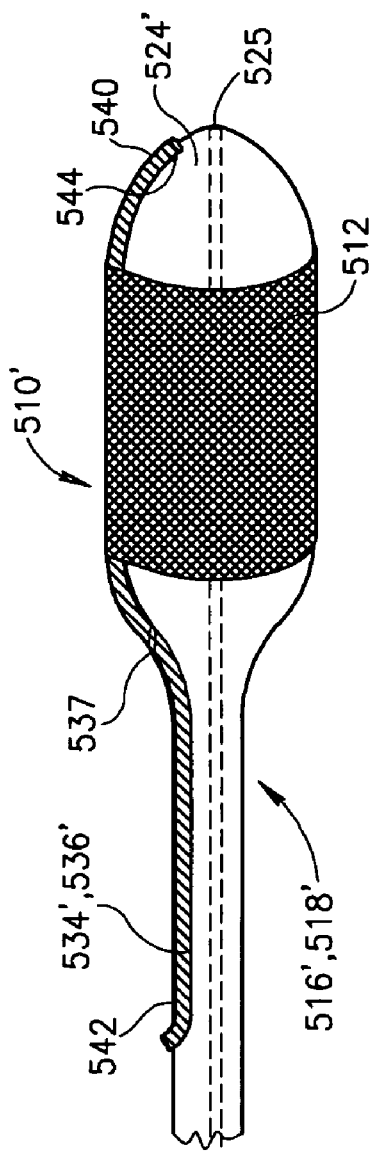
Figure 24C:
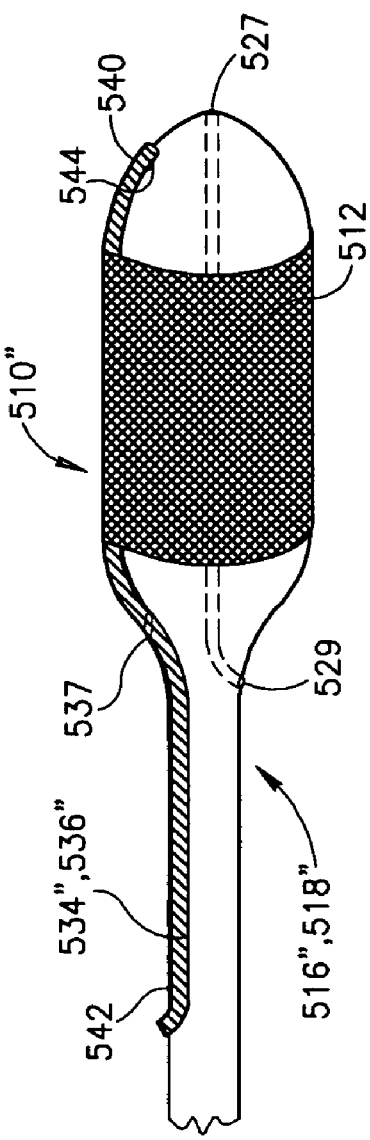

Reference is now made to FIGS. 24a-c, which are illustrations of different embodiments of a system 510 for delivery of a stent at a Type 3 bifurcation lesion. System 510 may be designed with a fixed wire, as shown in FIG. 24a, as on over-the-wire system, as shown in FIG. 24b, or as a rapid exchange system, as shown in FIG. 24c.

Reference is now made to FIG. 24a, which is an illustration of system 510 designed as a single wire system. System 510 includes a main elongated element 516 and an auxiliary elongated element 534. In a preferred embodiment, main elongated element 516 is a catheter 518. In a preferred embodiment, catheter 518 includes a balloon 524 with a fixed wire 526 at a distal end thereof. A stent 512 is positioned on balloon 524. In a preferred embodiment, auxiliary elongated element 534 is a guidewire lumen 536, and is attached to catheter 518 at a crotch point 544. Guidewire lumen 536 has a proximal end 542 and a distal end 540. Crotch point 544 is located at distal end 540. In a preferred embodiment, guidewire lumen 536 is positioned within catheter 518 proximally, exits at an exit point 537, and is attached to main elongated element 516 at crotch point 544. The portion of guidewire lumen 536 between exit point 537 and crotch point 544 may be attached or unattached. In a preferred embodiment, a distal end of guidewire lumen 536 is at crotch point 544, and a guidewire placed therethrough extends distally to provide a stopping point. In an alternative embodiment, the distal end of guidewire lumen is located 1-5 mm distal to crotch point 544, and is unattached to the catheter 518 in this location.

In one embodiment, guidewire lumen 536 is located external to and positioned alongside catheter 518 proximal to crotch point 544, and is unattached to elongated element 516 distal to crotch point 544. In an alternative embodiment, guidewire lumen 536 is unattached to catheter 518 both proximal to and distal to crotch point 544. Crotch point 544 is located at or near a distal end of stent 512. In a preferred embodiment, crotch point 544 is approximately 2-3 mm distal to the distal end of stent 512.

Figure 27A:
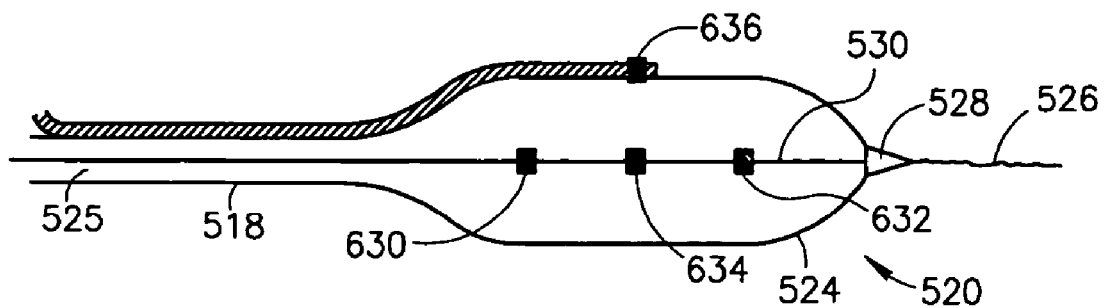
FIGS. 27a-d are illustrations of a configuration of markers.

Referring to FIG. 27a, in an exemplary preferred embodiment, balloon 524 is a fixed wire balloon and as such, includes a fixed wire 526 attached to a distal end of balloon 524 at a bonding area 528. A core wire 530 (or skeleton) runs along the interior of balloon 524 to provide rigidity to the flexible portion of catheter 518. Core wire 530 is a continuation of fixed wire 526. It is a particular feature of the present invention that core wire 530 is connected at a proximal end thereof to hypotube 525, at a distal end thereof to the distal end of balloon 524, and in at least one other location in between. Specifically, core wire 530 is bonded to catheter 518 at an area where guidewire lumen 536 exits catheter 518. Furthermore, core wire 530 is relatively thick as compared to a filament which is present within commercially available fixed wire balloons. Such filaments are typically within a range of 0.005 to 0.009 inches (most commonly around 0.007 inches), while the core wire 530 of the present invention is in a range of 0.009-0.012 inches (most preferably around 0.01 inches). This thickness, along with additional bonding of core wire 530 to catheter 518, provides rigidity along an entire length of catheter 518. This rigidity allows transmission of torque forces from proximal end 522 to distal end 520 of catheter 518, thus providing enhanced torqueability of the system. Furthermore, the rigidity provided by core wire 530 and the features described above provide enhanced pushing capability of the system of the present invention, by preventing absorption of pushing forces by the polymer jacket or by other relatively compliant portions of system 510.

Reference is now made to FIG. 24b, which is an illustration of system 510' designed as an over-the-wire, double rail system. System 510' is similar to system 510 shown in FIG. 25a, except that in place of a fixed wire on the distal end of balloon 524', a main guidewire lumen 525 is present and runs the length of catheter 518'. A main guidewire is positioned through main guidewire lumen 525 for entry into main vessel 1. System 510' may be introduced to the site via a main guidewire located in main guidewire lumen 525 or via a branch guidewire located in guidewire lumen 536'.

Reference is now made to FIG. 24c, which is an illustration of system 510", designed as a rapid exchange dual wire system. System 510" is similar to both systems 510 and 510' depicted in FIGS. 24a and 24c, except that in place of a fixed wire or a main guidewire lumen running the length of catheter 518", a short main guidewire lumen 527 is present and runs proximally until an exit point 529. In the present invention, the location of crotch point 544 allows for more accurate placement within the vessel.

Reference is now made to FIG. 25, which is a depiction of system 510 positioned at bifurcation 3 for a Type 3 lesion. A side branch guidewire 538 is introduced into branch vessel 2. System 510 is guided over side branch guidewire 538 and either fixed wire 526 or a main guidewire 539, depending on the type of system, until crotch point 544 of guidewire lumen 536 is at bifurcation point 3. In a preferred embodiment, distal end 540 is at crotch point 544, and only guidewire 538 enters branch vessel 2. In an alternative embodiment, guidewire lumen 536 extends into side branch vessel 2. System 510 is slowly advanced until crotch point 544 reaches bifurcation point 3, after which system 510 automatically stops advancing. Balloon 524 is then inflated, deploying stent 512. After deployment, balloon 524 is deflated, and system 510 is removed.

Reference is now made to FIG. 26, which is a depiction of system 510 positioned at a non-bifurcated lesion within a vessel 600. In one embodiment, a guidewire 610 is introduced into vessel 600 and through the lesion. System 510 is guided over guidewire 610 and fixed wire 526 until catheter 518 reaches the lesion site. Location is determined by markers 532, as will be described more fully hereinbelow with respect to FIGS. 27a-d and 28. Balloon 524 is then inflated, deploying stent 512. After deployment, balloon 524 is deflated, and system 510 is removed. By providing a guidewire in the vessel which is held in a guidewire lumen having an exit port distal to the proximal end of catheter 518, a rapid exchange of catheters is possible if necessary. Furthermore, the system can be used in a direct stenting procedure, without the need for predilatation, reducing the invasiveness of the procedure. In an alternative embodiment, guidewire 610 is backloaded and housed in guidewire lumen 536, and system 510 is introduced into the vessel guided by fixed wire 526. System 510 is suitable for crossing the lesion on its own due to the rigidity provided by core wire 530. Once system 510 is in place, guidewire 610 is advanced so that a backup wire is present at and distal to the lesion (for rapid exchange capabilities, for example). Balloon 524 is then inflated, deploying stent 512. There are several advantages in using system 510 as a regular non-bifurcation stent delivery system, over the typical delivery systems currently available. It is widely recognized that rapid exchange has certain advantages, including ease of delivery and ease of interchanging catheters if necessary. However, the presence of a bonded, relatively thick core wire allows for greater ease of rotation and transmission of torque forces without increasing overall diameter, which is advantageous during delivery of the system. Furthermore, in a direct stenting procedure, either guidewire 610 or fixed wire 526 is suitable for crossing the lesion. With fixed wire 526 crossing the lesion, stent 512 is automatically in place.

Figure 27B:
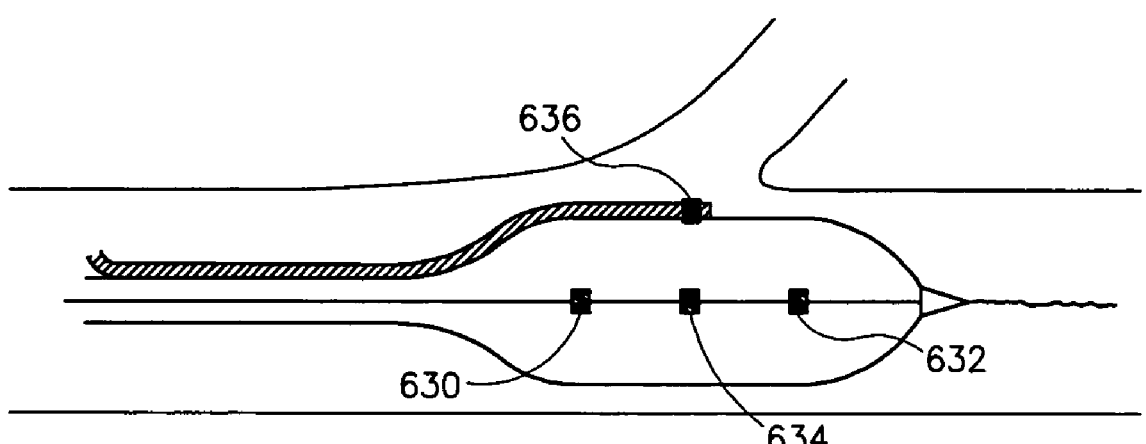
Figure 27C:
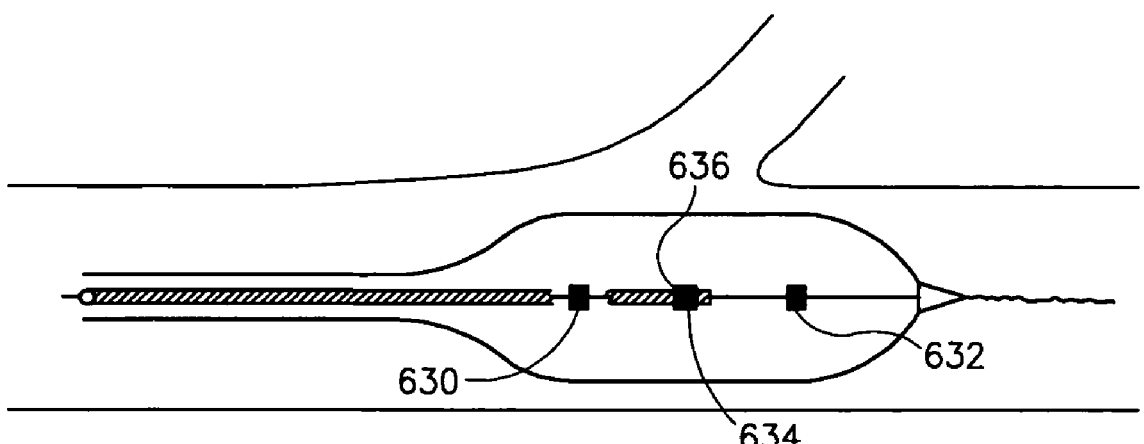
Figure 27D:
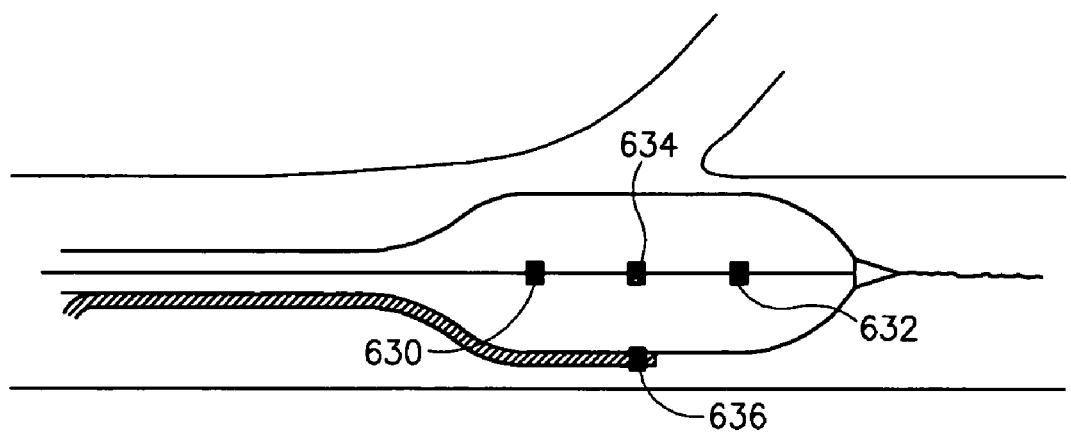
Figure 28:
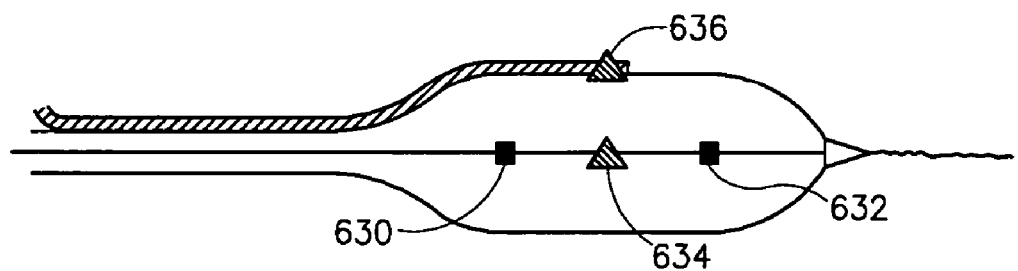
FIG. 28 is an illustration of a specific shape configuration of markers.

Reference is now made to FIGS. 27a-d, which are illustrations of a marker configuration, in accordance with a preferred embodiment. As shown in FIG. 27a, a first marker 630, a second marker 632 and a third marker 634 are included on core wire 30, and are aligned with proximal and distal ends of stent 12 and with crotch point 44, respectively. A fourth marker 636 is positioned at crotch point 44, thus forming a triangle with first and second markers 630 and 632. As shown in FIG. 27b, when system 10 is in position, the relative locations of the three markers are consistent with the original configuration. That is, first, second and third markers 630, 632 and 634 are aligned, and fourth marker 636 is off to one side. As shown in FIG. 27c, when system 10 is rotated 90 degrees, all four markers are relatively in the same line. As shown in FIG. 27d, when system 10 is rotated 180 degrees, fourth marker 636 is on the other side of first, second and third markers 630, 632 and 634. In this way, it is possible to visualize the rotational alignment of system 10 on a two-dimensional viewing screen. In addition, markers 634 and/or 636 may be configured in a triangle or pointing shape, as depicted in FIG. 28, pointing toward the branch access. This also provides additional confirmation of correct positioning. Thus, proper alignment at a bifurcation is ascertained when all the markers are correctly positioned with respect to one another, and when the pointing shaped marker points toward the branch.

Although the invention has been described in conjunction with specific embodiments thereof, it is evident that many alternatives, modifications and variations will be apparent to those skilled in the art. For example, a self-expandable stent may be used in place of a balloon expandable stent, in which case the catheter would not necessarily be a balloon catheter. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A catheter system comprising:
   a catheter body having a catheter proximal end and a catheter distal end, said catheter proximal end and said catheter distal end defining a longitudinal direction, said catheter proximal end comprising a rigid member;
   a balloon positioned at said catheter distal end and comprising:
      a working length portion having a substantially uniform diameter;
      a proximal narrowed portion proximal to said working length portion having a smaller diameter than said substantially uniform diameter of said working length portion;
      and a distal narrowed portion distal to said working length portion having a smaller diameter than said substantially uniform diameter of said working length portion;
   a wire extending from and unslidingly attached to said distal narrowed portion of said balloon, said wire configured for guiding said catheter through a vessel; and
   a guidewire enclosure having an enclosure proximal end and an enclosure distal end, said guidewire enclosure at least partially attached to said catheter at an attachment point, wherein said attachment point is located proximal to said working length portion of said balloon.

2. The catheter system of claim 1, wherein said attachment point is at a junction of said working length portion and said proximal narrowed portion.

3. The catheter system of claim 1, wherein said guidewire enclosure is at least partially positioned within said catheter body.

4. The catheter system of claim 1, wherein said attachment point is proximal to said enclosure distal end.

5. The catheter system of claim 1, wherein said attachment point is at said enclosure distal end.

6. The catheter system of claim 1, further comprising a guidewire positionable within said guidewire enclosure.

7. The catheter system of claim 1, wherein at least a portion of said catheter body is comprised of a rigid material thereby providing a rigid control area, and further comprising a substantially rigid core wire positioned through said fixed wire balloon and connecting a balloon distal end and said rigid control area.

8. The catheter system of claim 1, wherein said wire is detachable from said balloon upon inflation of said balloon.

* * * * *